US007139607B1

(12) United States Patent  
Shelchuk

(10) Patent No.: US 7,139,607 B1
(45) Date of Patent: Nov. 21, 2006

(54) ARRHYTHMIA DISCRIMINATION

(75) Inventor: Anne M. Shelchuk, San Rafael, CA (US)

(73) Assignee: Pacesetter, Inc., Sylmar, CA (US)

( * ) Notice: Subject to any disclaimer, the term of this patent is extended or adjusted under 35 U.S.C. 154(b) by 565 days.

(21) Appl. No.: 10/460,597

(22) Filed: Jun. 11, 2003

Related U.S. Application Data

(60) Provisional application No. 60/388,623, filed on Jun. 12, 2002, provisional application No. 60/389,053, filed on Jun. 12, 2002, provisional application No. 60/388,709, filed on Jun. 12, 2002, provisional application No. 60/388,784, filed on Jun. 12, 2002, provisional application No. 60/388,707, filed on Jun. 12, 2002.

(51) Int. Cl.
*A61N 1/362* (2006.01)
(52) U.S. Cl. .............................. 607/9; 607/14; 600/518
(58) Field of Classification Search .................. 607/4, 607/9, 14, 17, 25
See application file for complete search history.

(56) References Cited

U.S. PATENT DOCUMENTS

| | | | |
|---|---|---|---|
| 4,712,555 A | 12/1987 | Thornander et al. | 128/419 |
| 4,940,052 A | 7/1990 | Mann et al. | 128/419 |
| 4,944,298 A | 7/1990 | Sholder | 128/419 |
| 5,199,428 A | 4/1993 | Obel et al. | 128/419 |
| 5,203,326 A | 4/1993 | Collins | 128/419 |
| 5,243,980 A | 9/1993 | Mehra | 607/6 |
| 5,330,507 A | 7/1994 | Schwartz | 607/14 |
| 5,466,254 A | 11/1995 | Helland | 607/123 |
| 5,476,483 A | 12/1995 | Bornzin et al. | 607/17 |
| 5,507,784 A | 4/1996 | Hill et al. | 607/14 |
| 5,700,282 A | 12/1997 | Zabara | 607/6 |
| 5,836,974 A | 11/1998 | Christini et al. | 607/5 |
| 6,449,503 B1 * | 9/2002 | Hsu | 600/518 |
| 6,611,713 B1 * | 8/2003 | Schauerte | 607/14 |
| 6,687,540 B1 * | 2/2004 | Marcovecchio | 607/5 |
| 6,889,079 B1 * | 5/2005 | Bocek et al. | 607/9 |

FOREIGN PATENT DOCUMENTS

EP   1 106 206 A2   11/2000

OTHER PUBLICATIONS

Du et al., "Response to Cardiac Sympathetic Activation in Transgenic Mice Overexpressing $\beta_2$-Adrenergic Receptor," Amer. Phys. Soc., 1996; 0363-6135/96:H630-H636.
Mendelowitz, "Advances in Parasympathetic Control of Heart Rate and Cardiac Function," News Physio. Sci., 1999; 14:155-161.
Mizeres, "The Cardiac Plexus in Man[1]," Amer. J. of Anatomy, 1963; 112:141-151.
Murakami et al., "Effects of Cardiac Sympathetic Nerve Stimulation on the Left Ventricular End-Systolic Pressure-Volume Relationship and Plasma Norepinephrine Dynamics in Dogs," Jpn. Circ. J., 1997; 61:864-871.
Pauza et al., "Morphology, Distribution, and Variability of the Epicardiac Neural Ganglionated Subplexuses in the Human Heart", Anatomical Record, 2000; 259:353-382.
Wallick et al., "Separate Parasympathetic Control of Heart Rate and Atrioventricular Conduction of Dogs," Am. Phys. Society, 1990; 259(28):H536-H542.
Mazgalev et al., "Autonomic Modification of the Atrioventricular Node During Atrial Fibrillation Role in the Slowing of Ventricular Rate," Circulation, 1999; 99:2806-2814.

(Continued)

*Primary Examiner*—Carl Layno

(57) ABSTRACT

Various exemplary methods include altering conduction and/or operation of the AV node and/or AV bundle to help classify arrhythmias.

19 Claims, 18 Drawing Sheets

OTHER PUBLICATIONS

Mazgalev et al., "Anatomic-Electrophysiological Correlations Concerning the Pathways for Atrioventricular Conduction," Circulation, 2001; 103:2660-2667.

Paya et al., "Changes in Canine Ventricular Refractoriness Induced by Trains of Subthreshold High-Frequency Stimuli," J. Electrocardiology, 1991; 24(1):63-69.

Chen et al., "Intracardiac Stimulation of Human Parasympathetic Nerve Fibers Induces Negative Dromotropic Effects: Implication with the Lesions of Radiofrequency Catheter Ablation," J. Cardiovasc. Electrophysiol., Mar. 1998; vol. 9, No. 3: 245-252.

Lazzara et al., "Selective in Situ Parasympathetic Control of the Canine Sinoatrial and Strioventricular Nodes," Circulation Research, Mar. 1973, vol. XXXII:393-401.

Schauerte et al., "Ventricular Rate Control During Atrial Fibrillation by Cardiac Parasympathetic Nerve Stimulation: a Transvenous Approach," J. Am. College of Cardiology, 1999; vol. 34, No. 7:2043-2050.

Waninger et al., "Characterization of Atrioventricular Nodal Response to Electrical Left Vagal Stimulation," Annals of Biomedical Eng, 1999; vol. 27:758-762.

Kulboka et al., "Changes of Heart Electrophysiological Parameters After Destruction of Epicardial Subplexuses that Innervate Sinoatrial Node," Medicina, 2003; 39 Tomas, No. 6: 589-595.

* cited by examiner

continues on next page …

ARRHYTHMIA DISCRIMINATION

PRIORITY CLAIM AND CROSS-REFERENCE TO RELATED APPLICATIONS

The instant application claims priority to U.S. Provisional Applications: 1) Ser. No. 60/388,623, filed Jun. 12, 2002, entitled "Arrhythmia Discrimination", to Shelchuk; 2) Ser. No. 60/389,053, filed Jun. 12, 2002; 3) Ser. Nos. 60/388,709, filed Jun. 12, 2002; 4) 60/388,784, filed Jun. 12, 2002; 5) 60/388,707, filed Jun. 12, 2002; and 6) nonprovisional U.S. application Ser. No. 10/420,998, filed Apr. 21, 2003, entitled "Parasympathetic Nerve Stimulation for ICD and/or ATP Patients," to Shelchuk; all above applications are incorporated by reference herein.

The instant application is related to co-pending U.S. patent application having Ser. No. 10/460,013, filed Jun. 11, 2003, entitled "Vagal stimulation for improving cardiac function in heart failure or CHF patients", to Shelchuk, which is incorporated by reference herein and which claims priority to a U.S. Provisional Application having Ser. No. 60/388,709, filed Jun. 12, 2002, which is also incorporated by reference herein.

The instant application is related to co-pending U.S. patent application Ser. No. 10/460,149, filed Jun. 11, 2003, entitled "Parasympathetic Nerve Stimulation for Termination of Supraventricular Arrhythmias", to Sheichuk, which is incorporated by reference herein and which claims priority to a U.S. Provisional Application Ser. No. 60/388,784, filed Jun. 12, 2002, which is also incorporated by reference herein.

The instant application is related to co-pending U.S. patent application Ser. No. 10/460,145, filed Jun. 11, 2003, entitled "Parasympathetic Nerve Stimulation for Control of AV Conduction", to Shelchuk, Bornzin and Falkenberg, which is incorporated by reference herein and which claims priority to a U.S. Provisional Application having Ser. No. 60/389,053, filed Jun. 12, 2002, which is also incorporated by reference herein.

TECHNICAL FIELD

Exemplary methods and/or devices presented herein generally relate to cardiac pacing and/or stimulation therapy. Various exemplary methods and/or devices concern stimulating autonomic nerves, other nerves and/or tissue to affect operation and/or conduction of the AV node and/or AV bundle. In particular, such methods and/or devices optionally aid in classification of arrhythmias.

BACKGROUND

In a normal heart, cells of the sinoatrial node (SA node) spontaneously depolarize and thereby initiate an action potential. This action potential propagates rapidly through the atria (which contract), slowly through the atrioventricular node (AV node), the atriventricular bundle (AV bundle or His bundle) and then to the ventricles, which causes ventricular contraction. Thus, in a normal heart, ventricular rhythm relies on conduction of action potentials through the AV node and AV bundle.

Disruption of action potentials in an atrium and/or a ventricle can lead to arrhythmias. Arrhythmias are generally classified as supraventricular arrhythmias and ventricular arrhythmias. Supraventricular arrhythmias (SVAs) are characterized by abnormal rhythms that may arise in the atria or the atrioventricular node (AV node). For example, a paroxysmal SVA can exhibit heart rates between approximately 140 beats per minute (bpm) and approximately 250 bpm. However, the most common SVAs are typically atrial flutter and atrial fibrillation. In addition, many SVAs involve the AV node, for example, AV nodal reentry tachycardia (AVNRT) where an electrical loop or circuit includes the AV node.

Atrial flutter can result when an early beat triggers a "circus circular current" that travels in regular cycles around the atrium, pushing the atrial rate up to approximately 250 bpm to approximately 350 bpm. The atrioventricular node between the atria and ventricles will often block one of every two beats, keeping the ventricular rate at about 125 bpm to about 175 bpm. This is the pulse rate that will be felt, even though the atria are beating more rapidly. At this pace, the ventricles will usually continue to pump blood relatively effectively for many hours or even days. A patient with underlying heart disease, however, may experience chest pain, faintness, or even heart failure as a result of the continuing increased stress on the heart muscle. In some individuals, the ventricular rate may also be slower if there is increased block of impulses in the AV node, or faster if there is little or no block.

If the cardiac impulse fails to follow a regular circuit and divides along multiple pathways, a chaos of uncoordinated beats results, producing atrial fibrillation. Fibrillation commonly occurs when the atrium is enlarged (usually because of heart disease). In addition, it can occur in the absence of any apparent heart disease. In fibrillation, the atrial rate can increase to more than 350 bpm and cause the atria to fail to pump blood effectively. Under such circumstances, the ventricular beat may also become haphazard, producing a rapid irregular pulse. Although atrial fibrillation may cause the heart to lose approximately 20 to 30 percent of its pumping effectiveness, the volume of blood pumped by the ventricles usually remains within the margin of safety, again because the atrioventricular node blocks out many of the chaotic beats. Hence, during atrial fibrillation, the ventricle may contract at a lesser rate than the atria, for example, of approximately 125 bpm to approximately 175 bpm.

Overall, SVAs are not typically immediately life threatening when compared to ventricular arrhythmias. Ventricular arrhythmias include ventricular tachycardia and ventricular fibrillation, which typically originate in the ventricles. Ventricular arrhythmias are often associated with rapid and/or chaotic ventricular rhythms. For example, sustained ventricular tachycardia can lead to ventricular fibrillation. In sustained ventricular tachycardia, consecutive impulses arise from the ventricles at a rate of 100 bpm or more. Such activity may degenerate further into disorganized electrical activity known as ventricular fibrillation. In ventricular fibrillation, disorganized action potentials can cause the myocardium to quiver rather than contract. Such chaotic quivering can greatly reduce the heart's pumping ability. Indeed, approximately two-thirds of all deaths from arrhythmia are caused by ventricular fibrillation. A variety of conditions such as, but not limited to, hypoxia, ischemia, pharmacologic therapy (e.g., sympathomimetics), and asynchronous pacing may promote onset of ventricular arrhythmia.

As described above, SVAs and ventricular arrhythmias may lead to ventricular rates in excess of 100 bpm; hence, discrimination of ventricular arrhythmias from SVAs may require more than just knowledge of ventricular rate. In addition, most implantable stimulation devices do not have an ability to adequately discriminate between SVA and ventricular arrhythmias. Further, implantable devices having antitachycardia pacing, cardioversion stimulus and/or defibrillation shock capabilities may use such capabilities inappropriately to treat elevated ventricular rates originating from SVAs. Therefore, a need exists for methods and/or devices to discriminate between arrhythmias. Various exemplary methods and/or devices are described below which optionally address this need and/or other needs.

SUMMARY

According to various exemplary methods, delivery of one or more stimulation pulses affects conduction and/or operation of an AV node and/or AV bundle to help classify an arrhythmia. According to various exemplary methods, the delivery optionally occurs postinspiration. Various exemplary systems include one or more sensors configured to sense ventricular rhythm, one or more stimulation electrodes positionable proximate to the AV node and/or AV bundle and/or one or more stimulation electrodes positionable proximate to a parasympathetic nerve. An exemplary system includes a stimulation device configured to detect ventricular rhythm; to deliver one or more stimulation pulses to the AV node, the AV bundle, and/or a parasympathetic nerve; and to classify a ventricular rhythm as a ventricular arrhythmia and/or a supraventricular arrhythmia.

Various exemplary devices for performing such exemplary methods are also disclosed herein along with a variety of other exemplary methods and/or devices. In general, the various devices and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate nerves and/or stimulate and/or shock a patient's heart.

Figure 1:
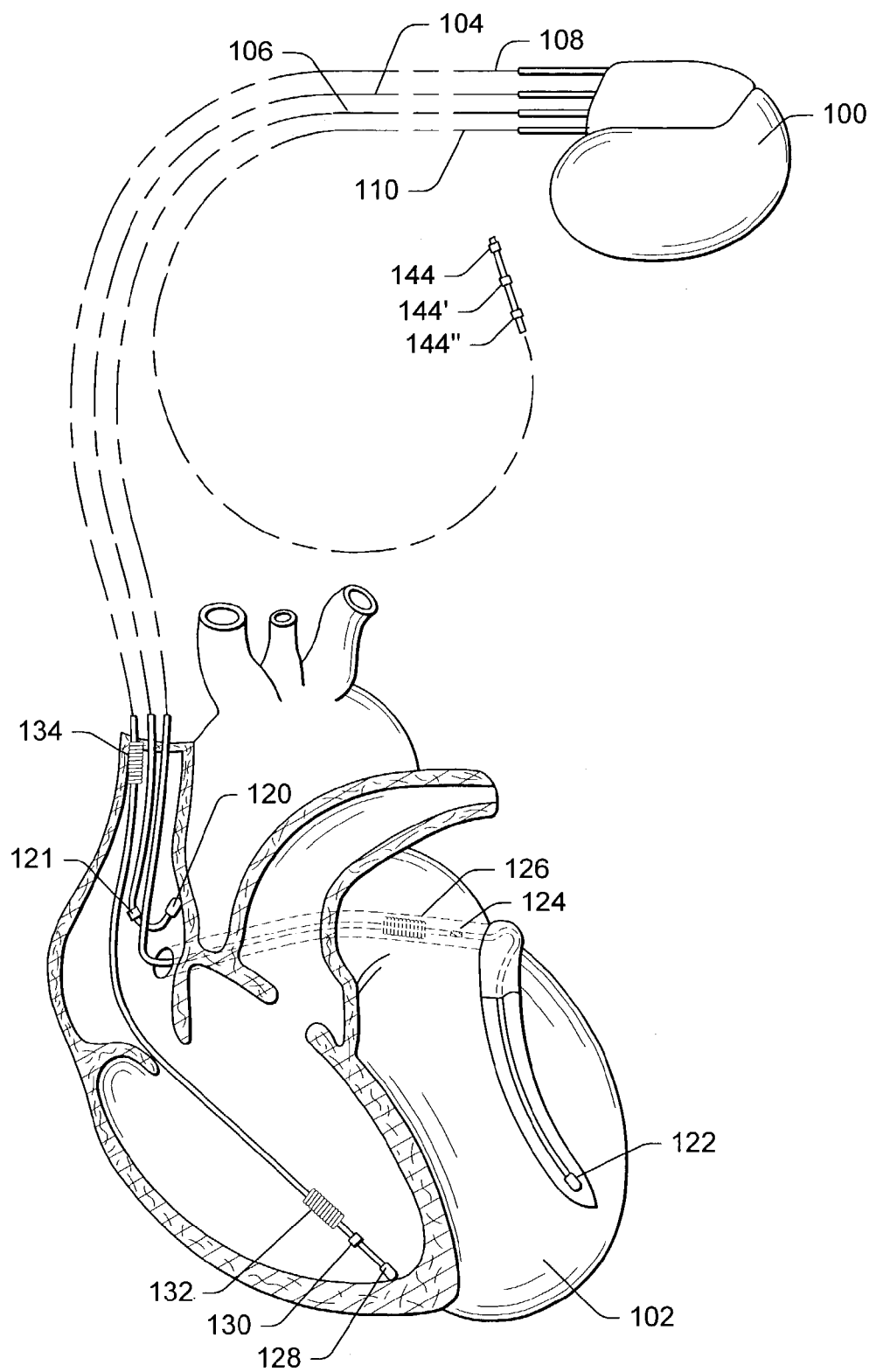
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
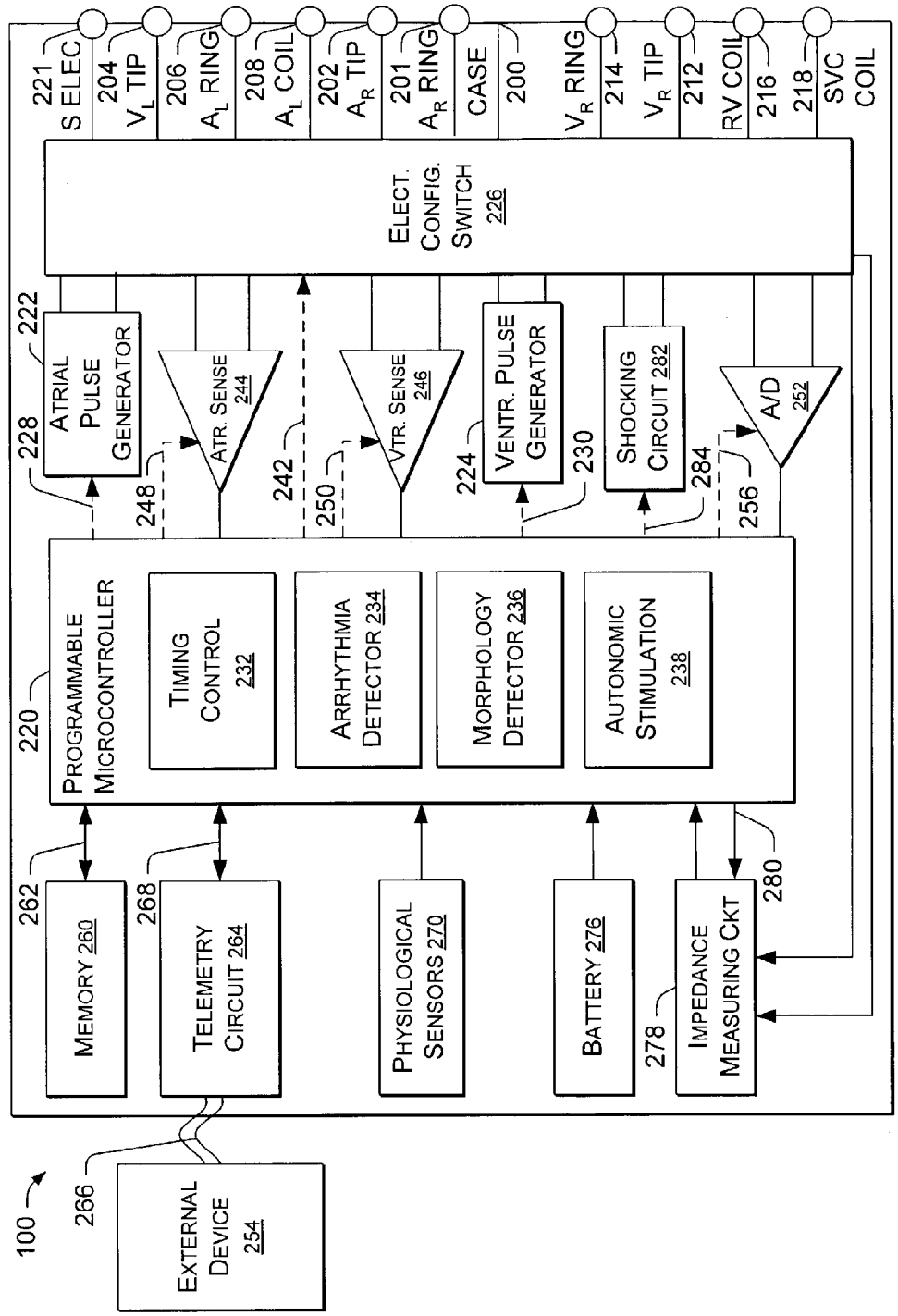
FIG. 2 is a functional block diagram of an exemplary implantable stimulation device illustrating basic elements that are configured to provide cardioversion, defibrillation, pacing stimulation and/or autonomic nerve stimulation or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal (AR TIP) 202 adapted for connection to the atrial tip electrode 120. A right atrial ring terminal (AR RING) 201 is also shown, which is adapted for connection to the atrial ring electrode 121. To achieve left chamber sensing, pacing, shocking, and/or autonomic stimulation, the connector includes at least a left ventricular tip terminal (VL TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an autonomic nerve stimulation module 238 for performing a variety of tasks related to autonomic nerve stimulation. This component can be utilized by the stimulation device 100 for determining desirable times to administer various therapies, including, but not limited to, parasympathetic stimulation. The autonomic module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

AV Node and AV Bundle

As already mentioned, in a normal heart, cells of the sinoatrial node (SA node) spontaneously depolarize and thereby initiate an action potential. This action potential propagates rapidly through the atria (which contract), slowly through the atrioventricular node (AV node), the atriventricular bundle (AV bundle or His bundle) and then to the ventricles, which causes ventricular contraction. Thus, in a normal heart, ventricular rhythm relies on conduction of action potentials through the AV node and AV bundle.

The AV node is a small subendocardial structure within the interatrial septum, anterior and superior to the coronary sinus, located at the convergence of specialized conduction tracts that course through the atria. The AV node has extensive autonomic innervation and an abundant blood supply from the large AV nodal artery, which is a branch of the right coronary artery in approximately 90 percent of the population, and from septal branches of the left anterior descending coronary artery (circumflex artery). The AV node forms part of the only "normal" electrical connection between atria and ventricles. While various conduction subpathways may exist in the AV node or AV nodal region, the AV node is known to transmit impulses slowly via at least one pathway, e.g., requiring approximately 60 ms to approximately 130 ms to traverse about 1 cm of node tissue. In general, slowing of an impulse by AV nodal tissue protects the ventricles by typically not allowing all impulses through, which, in turn, prevents the ventricles from racing in response to a rapid atrial rhythm (see, e.g., Background section). Under some circumstances, the AV node blocks all impulses to the ventricles. Further, clinical ablation of the AV node can also block all impulses to the ventricles.

En route to the ventricles, action potentials pass via Purkinje fibers, which typically emerge from the distal region of the AV node and converge gradually to form at least part of the AV bundle. Blood supplies the AV bundle from the AV nodal artery and septal branches of the left anterior descending artery. The AV bundle has relatively sparse autonomic innervation and is somewhat encased within a collagenous skeleton. Destruction of the AV bundle, for example, through ablation, may also block all impulses to the ventricles.

While ablation of a patient's AV node and/or AV bundle has been shown to block unwanted conduction of action potentials to the ventricles, these procedures are irreversible; thus, a need exists to slow and/or block action potentials in a reversible manner. As described herein, various exemplary methods and/or exemplary devices optionally stimulate nerves to effectively slow and/or block conduction of action potentials through a patient's AV node and/or AV bundle. Further, various exemplary methods and/or devices accomplish such tasks in a reversible manner. Various exemplary methods and/or devices use reversible AV block or slowing to discriminate between arrhythmias.

As already mentioned, the AV node and the AV bundle play important roles in conduction of action potentials to the ventricles. Further, conduction of action potentials may occur via one or more pathways. A recent report by Mazgalev et al., "Anatomic-electrophysiological correlations concerning the pathways for atrioventricular conduction", *Circulation*, 103:2660–2667 (2001), discusses what have traditionally been referred to as "slow" and "fast" conduction pathways.

Figure 3:
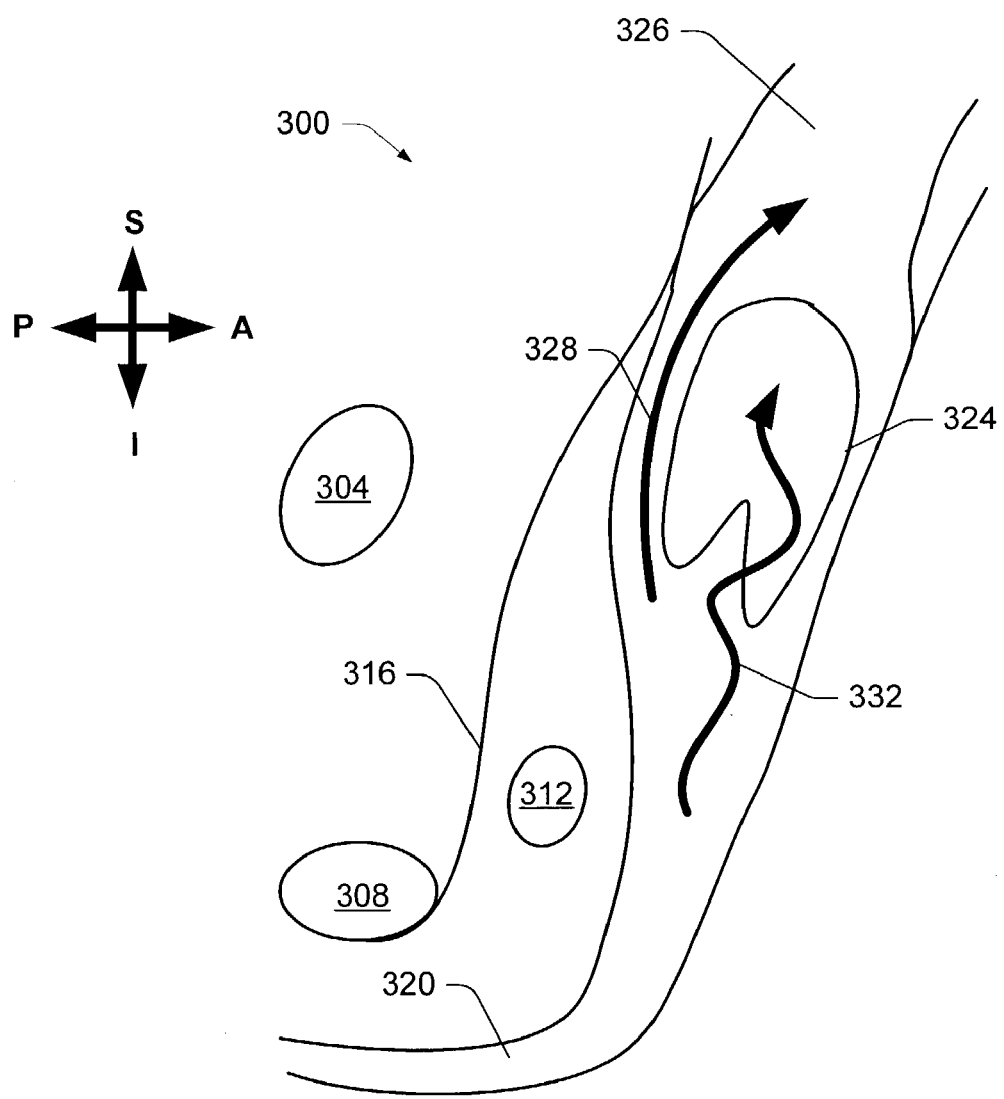
FIG. 3 is an approximate anatomical diagram of an AV nodal region including an AV node and at least part of an AV bundle.

Referring to FIG. 3, an approximate anatomical diagram of the AV nodal region 300 including the AV node and at least part of the AV bundle is shown. As shown, the AV nodal region 300 includes several anatomical landmarks such as the fossa ovalis 304, the inferior vena cava 308, the coronary sinus 312, the tendon of Todaro 316, and the crista terminalis 320. In addition, a directional indicator indicates approximate anatomical directions: "S" superior, "I" inferior, "P" posterior, and "A" anterior. An approximate AV node 324 is also shown, including inferior nodal extensions that lead into a compact cell region, and an AV bundle 326. A "fast" pathway 328 is shown along with a "slow" pathway 332. In FIG. 3, both pathways 328, 332 are oriented primarily from inferior to superior and secondarily from posterior to anterior.

As described by Mazgalev et al., conduction along the slow pathway 332 proceeds from the inferior nodal extensions and through the lower nodal cells, which leads to a superior region of compact cells and on to the AV bundle 326. Mazgalev et al., indicate that the term "slow" seems appropriate because "the pathway [332] encompasses the entire length of the nonpenetrating axis and that the pathway is composed or nodal or nodal-like cells with specific electrophysiological properties that are responsible for a slow velocity of conduction". Mazgalev et al., further note that "the clinical procedure of slow pathway ablation, which is performed in the isthmus between the coronary sinus and the tricuspid valve, may not necessarily eliminate the slow pathway domain" and "may inflict its damage on the plain atrial tissue forming the gap between the inferior nodal approaches and the node itself"; hence, "slow pathway ablation may very well coexist with preservation of the dual-pathway electrophysiology, as has been demonstrated clinically". Therefore, Mazgalev et al., also points to some of the shortcomings associated with "slow pathway ablation".

Regarding the "fast" pathway, Mazgalev et al., state that propagation of an action potential "proceeds toward the most superior extensions of the transitional cells". In FIG. 3, the transitional cells are located within a transitional envelope that extends inferiorly from the inferior nodal extensions and generally surrounds the AV node 324 to even some superior points, e.g., where the tendon 316 joins near the bundle region 326. Such an action potential may form a short transverse route through, for example, a portion of the compact region and into the AV bundle 326. Mazgalev et al., note that while "it may be extremely difficult to ablate the fast pathway selectively . . . lesions on the transitional envelope, especially where it comes in close contact with the compact cells, are likely to produce conduction block".

Mazgalev et al., further note that the slow and fast pathways are not insulated and therefore, "intercommunication between wavefronts can be expected". Consequently, a "fast wavefront running on the surface can exert an electronic depressive effect on the deeper nodal structures"

and "ablation of a slow pathway may modulate the refractory properties of the remaining fast wavefront".

In general, AV conduction blocks are categorized as first-degree, second-degree and third-degree. First-degree block is associated with P wave to R wave prolongation (e.g., greater than approximately 0.2 s) with all P waves followed by QRST. Second-degree block is often classified as type I (Wenckebach), type II or high-grade. Type II involves intermittent blocking of P waves with constant P-R intervals. For example, a 2:1 AV block has constant P-R intervals with every second P wave blocked. In high-grade, two or more successive P waves are blocked and, in general, the atrial rate exceeds the ventricular rate. Third-degree block is associated with complete dissociation of P waves and QRST complexes, and, in general, the atrial rate exceeds the ventricular rate.

As described herein, various exemplary methods and/or devices stimulate nerves and/or tissue to cause some degree of reversible block. Accordingly, stimulation may occur at one or more site proximate to and/or remote from the AV nodal region, including the AV bundle. Various exemplary methods and/or devices stimulate autonomic nerves, other nerves and/or tissue to cause some degree of block. In various exemplary methods and/or devices presented herein, the term atrio-ventricular node may include at least part of an atrio-ventricular bundle.

Nerve/Tissue Stimulation Affects AV Node and/or AV Nodal Region

The tissue of the AV node and/or AV nodal region may be depolarized and/or made to respond more slowly through application of one or more electrical and/or magnetic stimuli. While such a mechanism may stimulate parasympathetic nerves, for example, resulting in the release of acetylcholine, the main thrust of such stimuli is to decrease conduction in the AV node and/or AV nodal region. For example, Paya et al., "Changes in canine ventricular refractoriness induced by trains of subthreshold high-frequency stimuli", *J. Electrocardiology*, 24(1):63–69 (1991), reported that subthreshold conditioning decreased myocardial ventricular excitability, prolonging the effective ventricular refractory period in direct proportion to the subthreshold pulse frequency. Thus, subthreshold stimulation during non-refractory and/or refractory periods of the AV node and/or AV nodal region and/or greater stimulation (e.g., at or above threshold) during a refractory period are optionally used to adjust conduction via the AV node and/or AV nodal region. Of course, stimulation at or above threshold is optionally used during a non-refractory period to cause an evoked response and to affect conduction of the AV node and/or AV nodal region.

In one example, an electrode is positioned proximate to the AV node and used to deliver stimuli to decrease conduction in the AV node and to cause an evoked response of one or more chambers of the heart. Such an electrode may be used in a manner to cause an evoked response when target myocardium is not refractory and to decrease conduction in the AV node when the target myocardium is refractory. Of course, such an electrode may stimulate a parasympathetic nerve that acts to decrease AV nodal conduction as well. Various exemplary methods optionally use such an electrode to alter AV conduction and/or to stimulate a chamber of the heart.

Parasympathetic Stimulation Affects AV Node and/or AV Nodal Region

Regarding the AV node, a study by Mazgalev et al., "Autonomic modification of the atrioventricular node during atrial fibrillation: role in the slowing of ventricular rate", *Circulation*, 99:2806–2814 (1999), reported that "postganglionic vagal stimulation (PGVS) by short bursts of subthreshold current evokes release of acetylcholine from myocardial nerve terminals" and that "PGVS applied to the atrioventricular node slows nodal conduction". Overall, Mazgalev et al., recognized various attempts at AV node modification (to slow ventricular rate while preserving AV nodal function), noted "inconsistent success rates among investigators", and stated "if this [AV node modification] is unsuccessful, complete AV node destruction can be performed, rendering the patient pacemaker-dependent and undesirably altering the normal sequence of ventricular activation". The goals elaborated by Mazgalev et al., were specifically directed to slowing ventricular rate during atrial fibrillation. As described herein, various exemplary methods and/or devices optionally include parasympathetic, other nerve and/or tissue stimulation to affect the AV node and/or AV nodal region to cause at least some degree of block under a variety of conditions, including those unrelated to atrial fibrillation.

A study by Wallick et al., "Separate parasympathetic control of heart rate and atrioventricular conduction of dogs", *Am J. Physiol.*, 259(2 Pt 2):H536–42 (1990), reported that the "inferior vena cava-inferior left atrial fat pad . . . contains nerves that innervate the AV node" and that stimulation of this "fat pad" elicited "a bimodal increase in the atrioventricular conduction time without eliciting any change in the cardiac cycle length". Wallick et al., also noted that they "found an occasional increase in AV conduction time in response to RPV fat pad stimulation", which may be due to "preganglionic fibers that synapse with the parasympathetic ganglia in the IVC-ILA fat pad also pass through or come within close proximity to the RPV fat pad". As described herein, various exemplary methods and/or devices optionally include stimulation of parasympathetic nerves to affect AV node and/or AV nodal regions to cause some degree of block.

Autonomic Nervous System

The autonomic nervous system includes sympathetic and parasympathetic pathways. Both pathways include afferent pathways (e.g., from an organ to central neurons) and efferent pathways (e.g., postganglionic neurons from ganglia to an organ) that relate to functioning of the heart. For example, parasympathetic efferent postganglionic neurons, when stimulated, suppress atrial rate and contractile force, atrio-ventricular nodal conduction, and ventricular contractile force, also known as contractility or inotropy. Sympathetic efferent postganglionic neurons, when stimulated, generally increase heart rate and increase contractility. Note that contractility is associated with the term "inotropy", heart rate is associated with the term "chronotropy" and conduction velocity is associated with the term "dromotropy".

As already mentioned, the stimulation of parasympathetic nerves can act to decrease heart rate while stimulation of sympathetic nerves can act to increase heart rate. In addition, as noted by Mendelowitz, "Advances in parasympathetic control of heart rate and cardiac function", *News Physiol. Sci.*, 14:155–161 (1999), "when both parasympathetic and sympathetic activity are present, parasympathetic activity generally dominates" and "increases in parasympathetic activity to the heart evoke a bradycardia that is more pronounced when there is a high level of sympathetic firing". Mendelowitz also noted that "the release of acetylcholine from parasympathetic neurons might act presynaptically to inhibit the release of norepinephrine from sympathetic nerve terminals".

Regarding sympathetic stimulation, norepinephrine is released by sympathetic nerves. After its release, norepinephrine acts on the sinoatrial node (SA node) to increase the rate of diastolic depolarization, and thereby increase heart rate, and acts on the atrioventricular node (AV node) to increase the velocity of conduction and diminish the refractory period during which the AV node is unresponsive to stimuli coming from the atrium.

Contractility (or inotropy) refers to the force or strength of cardiac muscle contractions. Stimulation of sympathetic nerves causes active contractility whereas Frank-Starling mechanism causes passive contractility. Active contractility involves norepinephrine, which increases myocardial calcium permeability (or conductance) and hence actin/myosin crossbridge interactions. Other mechanisms may also accompany the increase in calcium permeability.

In general, an increase in ventricular contractility causes an increase stroke volume, which, in turn, can increase cardiac output. Cardiac output (CO) depends on heart rate (HR) and stroke volume (SV) (e.g., CO equals HR times SV). Changes in ventricular contractility alter the rate of force and pressure development by the ventricle and therefore change the rate of ejection (i.e., ejection velocity). For example, an increase in contractility shifts the Frank-Starling curve, which causes a reduction in end-systolic volume and an increase in stroke volume. The increased stroke volume also causes a reduction in ventricular end-diastolic volume (i.e., preload). The end-systolic pressure-volume relationship (ESPVR) may define an inotropic state of the ventricle.

Changes in inotropic state are particularly important during exercise. Increases in inotropic state helps to maintain stroke volume at high heart rates. Increased heart rate alone decreases stroke volume because of reduced time for diastolic filling (decreased end-diastolic volume). When inotropic state increases at the same time, this decreases end-systolic volume to maintain stroke volume.

Another term used to describe cardiac operation is "cardiac workload", which is sometimes defined as the product of systolic blood pressure and heart rate. In general, an increase in inotropy, chronotropy and/or dromotropy result in an increase in cardiac workload. Further, sympathetic activity is likely to increase cardiac workload whereas parasympathetic activity is likely to decrease cardiac workload.

Figure 4:
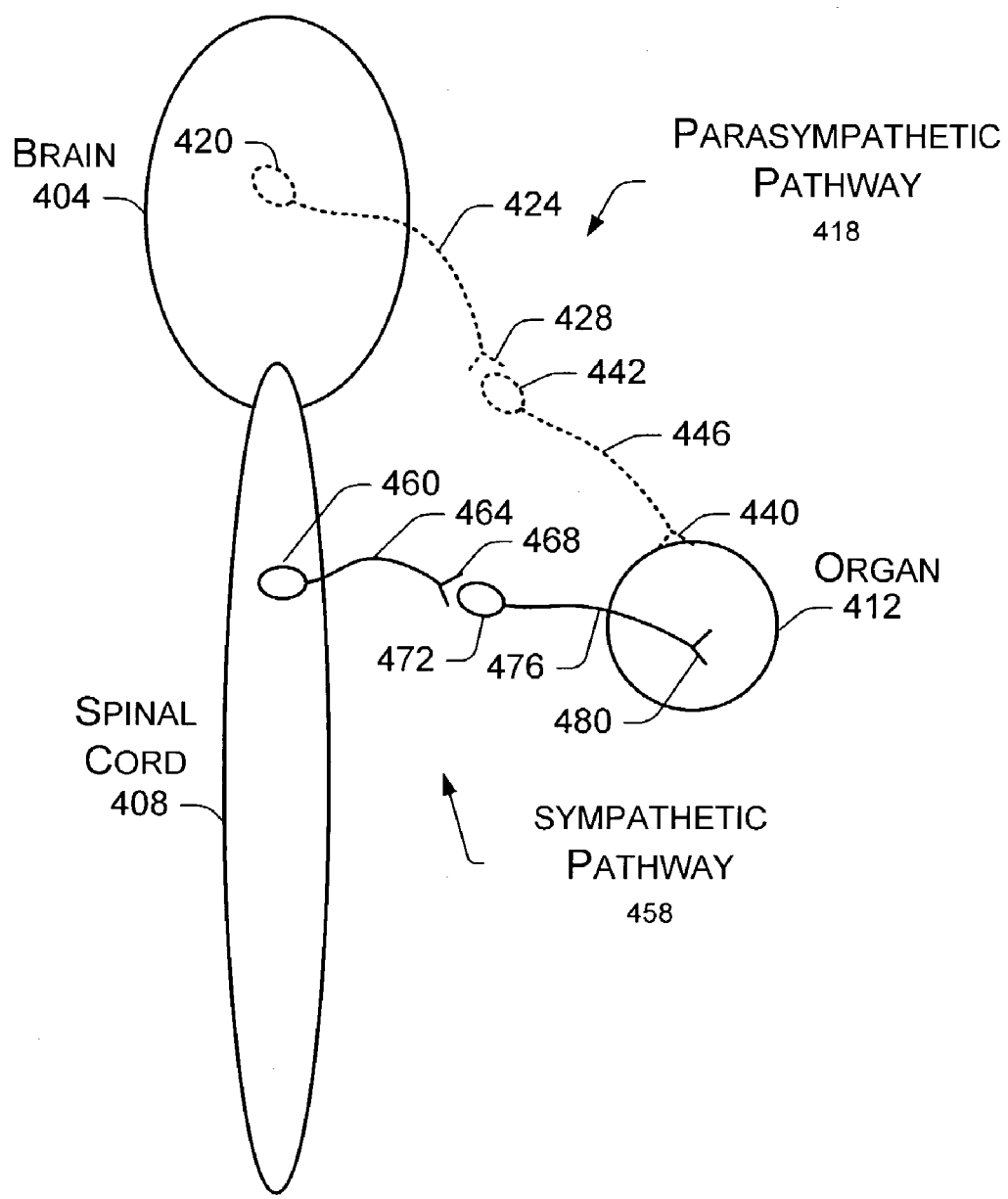
FIG. 4 is a simplified approximate anatomical diagram of a parasympathetic pathway and a sympathetic pathway of the autonomic nervous system.

As already mentioned, the autonomic nervous system includes parasympathetic and sympathetic pathways. Referring to FIG. 4, a simplified diagram of the autonomic nervous system 400 is shown. The system 400 illustrated includes a brain 404, a spinal cord 408, an organ 412, a parasympathetic efferent pathway 418 and a sympathetic efferent pathway 458. The parasympathetic efferent pathway 418 includes a preganglionic cell body 420 located in the brain 404, a preganglionic axon 424, a synaptic cleft 428, a postganglionic cell body 432, a postganglionic axon 436, and a postganglionic synaptic cleft 440 proximate to the organ 412. An exemplary parasympathetic stimulus originates at the brain 404 and ends at the postganglionic synaptic cleft 440 wherein a chemical is emitted to effect cell of the organ 412. A synaptic cleft may also be referred to as a neuroeffector junction. The sympathetic efferent pathway 458 includes a preganglionic cell body 460 located in the spinal cord 408, a preganglionic axon 464, a synaptic cleft 468, a postganglionic cell body 472, a postganglionic axon 476, and a postganglionic synaptic cleft 480 proximate to the organ 412. An exemplary sympathetic stimulus originates at the spinal cord 408 and ends at the postganglionic synaptic cleft 480 wherein a chemical is emitted to effect cell of the organ 412. In both pathways 418, 458, acetylcholine operates as a neurotransmitter to activate postganglionic neurons, i.e., preganglionic neurons are cholinergic. In parasympathetic pathways (e.g., the parasympathetic pathway 418), postganglionic neurons emit acetylcholine and are therefore cholinergic. However, in many sympathetic pathways (e.g., the sympathetic pathway 458), postganglionic neurons emit norepinephrine and are therefore adrenergic. While FIG. 4 shows a one to one ratio of preganglionic to postganglionic neurons, note that a preganglionic neuron generally links to more than one postganglionic neuron, for example, in a sympathetic pathway, a preganglionic neuron to postganglionic neuron ratio may be approximately 1:32. Autonomic pathways than can affect cardiac operation are described in more detail below.

Autonomic Pathways

As already mentioned, the autonomic nervous system includes both sympathetic and parasympathetic nerves. In general, the sympathetic nerves and parasympathetic nerves follow pathways, which, as described in more detail below, are at times to some degree intermingled. Intermingling in the vagosympathetic trunks includes, for example, fibers having a sympathetic core surrounded by a parasympathetic vagal skin. Such "vagosympathetic" fibers may arise from one of the vagosympathetic trunks and descend into epicardial and/or endocardial fibers of the heart. Parasympathetic pathways effecting cardiac operation include the vagus nerve, which is a member of a group of nerves commonly referred to as the cranial nerves. Scientifically, the vagus nerve has been designated as the tenth cranial nerve. There are two of these mixed nerves that act to provide both motor and sensory functions. Each vagus nerve contains both somatic and autonomic branches; however, the autonomic function predominates. Vagus nerves are parasympathetic in nature making up 75% of all parasympathetic fibers passing to the thoracic and abdominal regions of the body. As is the case with most nerves, vagi nerves contain both efferent fibers (e.g., to carry an impulse from its origin in the medulla obligata of the brain to a tissue or an organ), as well as afferent fibers, (e.g., to carry an impulse from a tissue or an organ back to the brain). With vagus nerves, 80% of the fibers are afferent as opposed to efferent. This aids in their active response to the many reflex actions in the body during parasympathetic control. As a whole, the two vagus nerves are very large and work to stimulate a great number of tissues in the body. Vagal stimulation can affect the heart, lungs, esophagus, stomach, small intestine, liver, gall bladder, as well as the upper portions of the ureters.

In general, the right and left vagus nerve pass down the neck as part of right and left vagosympathetic trunks. The right and left vagus also have branches that innervate the heart and lungs. Further down, the left vagus and the right vagus bifurcate into respective left and right ventral and left and right dorsal vagal branches which eventually join. The left and right ventral vagal branches join together to form the ventral vagal trunk on the ventral esophagus while the left and right dorsal vagal branches join together along the dorsal esophagus to form the dorsal vagal trunks. These vagal trunks pass through the esophageal hiatus of the diaphragm and supply the stomach, small intestine, part of the large intestine and major cranial abdominal viscera with parasympathetic innervation. The vagus also includes the right and left recurrent laryngeal nerves, which are somatic, primarily motor subdivisions of the vagus that travel down the neck as part of the right and left vagosympathetic trunks.

Upon stimulation, a vagus nerve releases the hormone acetylcholine at its vagal endings and is, therefore, cholinergic. This is in contrast with adrenergic systems which cause the release of epinephrine and norepinephrine. It is the release of acetylcholine, rather than the passing of nerve impulses that directly initiates a specific response. In general, the release of acetylcholine, rather than the passing of nerve impulses, initiates a specific response at an organ (e.g., the heart, etc.), recognizing that parasympathetic input to the brain is typically associated with a more complex mechanism, which may occur depending on stimulation site and/or stimulation parameters.

Regarding the heart, parasympathetic vagi nerves are distributed to regions of the SA node and the AV node. Release of acetylcholine to these regions typically results in both a decrease in the rate of rhythm of the SA node, as well as a decrease in the cardiac impulse transmission into the ventricles. Consequences of these actions generally include a decrease in heart rate, cardiac output, ventricular contraction, arterial blood pressure, as well as a decrease in overall ventricular pumping.

In general, the right vagus innervates the S-A nodal region, the atrial muscle and, to a much lesser degree, the A-V nodal region; whereas, the left vagus nerve innervates the S-A nodal region and atrial muscle to a lesser degree than it innervates the A-V nodal region. Stimulation of the right vagus nerve can predominately slow the S-A node rate and thereby reduces heart rate; whereas, stimulation of the left vagus nerve can produce some slowing of the S-A node, prolongation of A-V conduction and partial or total A-V block.

The vagi nerves are also involved in a process known as respiratory sinus arrhythmia (RSA). As stated in Mendelowitz, "Advances in parasympathetic control of heart rate and cardiac function", *News Physiol. Sci.,* 14:155–161 (1999), in RSA, "the heart beats more rapidly in inspiration and slows during postinspiration and expiration". Further, Mendelowitz noted that "cardiac vagal neurons recorded in vivo receive inhibitory synaptic input during inspiration, which is then followed by a rapid depolarization caused by excitatory synaptic input during postinspiration".

Figure 5:
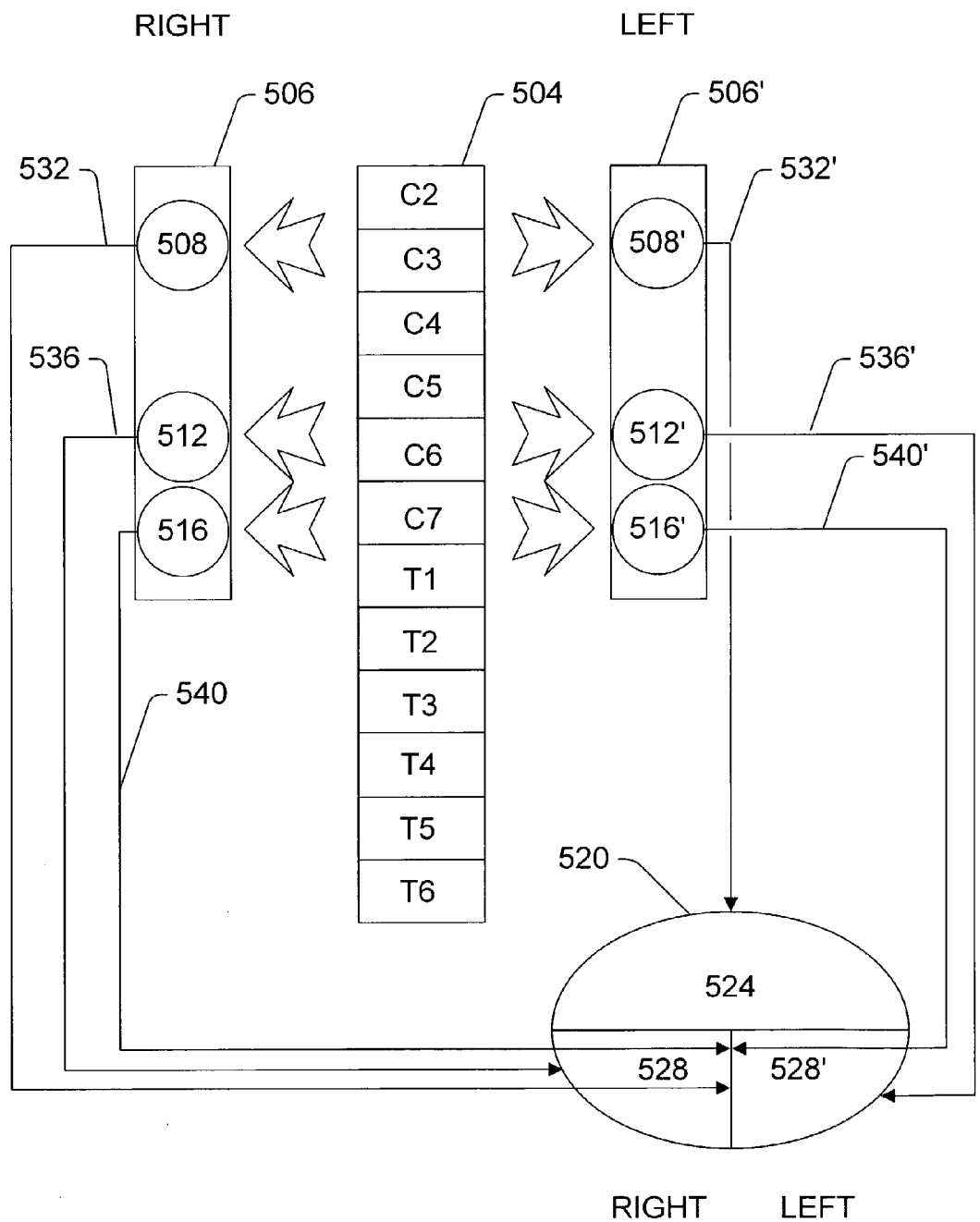
FIG. 5 is a simplified approximate anatomical diagram of sympathetic pathways and/or parasympathetic pathways to the heart.

Referring to FIG. 5, a block diagram of various components of the autonomic nervous system is shown. While FIG. 5 pertains primarily to sympathetic pathways, as already mentioned, intermingling of sympathetic pathways and parasympathetic pathways typically occurs to some degree at various points. The sympathetic nervous system, which is not part of the central nervous system, includes two parallel chains or trunks, a right trunk 506 and a left trunk 506'. Each trunk includes a series of ganglia which lie just lateral to the spinal cord 504 on each side (left and right). In general, the uppermost region of each trunk (506, 406') has three cervical ganglia, which are continuous with the thoracic trunk. The cervical ganglia are known as the right and left superior cervical ganglia (508, 508'), the right and left middle cervical ganglia (512, 512') and the right and left inferior cervical ganglia (516, 516'), the latter of which are known as a stellate ganglion if they combine with a respective first thoracic ganglion. Stellate ganglia exist in approximately 70% to approximately 80% of the population.

Cardiac sympathetic fibers originate in intermediolateral columns of the upper five or six thoracic segments (see T1–T6 in FIG. 5) and lower one or two cervical segments (see C5 and C6 in FIG. 5) of the spinal cord 504. Sympathetic fibers enter the paravertebral chain and typically synapse in the cervical ganglia. Cardiac sympathetic ganglia are generally found close to the spinal column (paravertebral ganglia) and may stem from both thoracic and cervical preganglionic fibers. Postganglionic cardiac sympathetic nerves originate from the left and right ganglia and usually approach the base of the heart (e.g., as superior, middle, and inferior cardiac nerves) along the adventitial surface of the great vessels.

Each of the superior cardiac nerves 532, 532' arises by two or more branches from a respective superior cervical ganglion 508, 508', and occasionally receives a filament from the trunk between a first and/or a second cervical ganglia. The right superior cardiac nerve 532, at the root of the neck, passes either in front of or behind the subclavian artery, and along the innominate artery to the back of the arch of the aorta, where it joins the deep part 528, 528' of the epicardial plexus 520. The right superior cardiac nerve 532 connects with other sympathetic branches. About the middle of the neck the right superior cardiac nerve 532 receives filaments from the external laryngeal nerve; lower down, one or two twigs from the vagus; and as it enters the thorax it is joined by a filament from the recurrent nerve. In addition, filaments from the nerve communicate with the thyroid branches from the right middle cervical ganglion 512. The left superior cardiac nerve 532', in the thorax, runs in front of the left common carotid artery and across the left side of the arch of the aorta, to the superficial part 524 of the epicardial plexus 520.

Each of the middle cardiac nerves 536, 536' (or great cardiac nerves), the largest of the three cardiac nerves, arises from a respective middle cervical ganglion 512, 512', or from a respective trunk 506, 506' between the middle ganglion 512, 512' and the inferior ganglion 516, 516'. On the right side, the right middle cardiac nerve 536 descends behind the common carotid artery, and at the root of the neck runs either in front of or behind the subclavian artery; it then descends on the trachea, receives a few filaments from the recurrent nerve, and joins the right half of the deep part 528 of the epicardial plexus 520. In the neck, it communicates with the right superior cardiac nerve 532 and recurrent nerve. On the left side, the left middle cardiac nerve 536' enters the chest between the left carotid and subclavian arteries, and joins the left half of the deep part 528' of the epicardial plexus 520.

Each inferior cardiac nerve 540, 540' arises from the respective inferior cervical ganglion 516, 516' or the first thoracic ganglion (or stellate ganglion, e.g., 516, 516'). Both right and left inferior cardiac nerves 540, 540' descend behind the subclavian artery and along the front of the trachea, to join the deep part 528, 528' of the epicardial plexus 520. Each of the inferior cardiac nerves 540, 540' communicates freely behind the subclavian artery with the recurrent nerve and the respective middle cardiac nerve 536, 536'.

As already mentioned with reference to FIG. 5, at the base of the heart, the sympathetic fibers form an epicardial plexus 520 that distributes the fibers to the various regions of the heart. The epicardial plexus 520 has a superficial part 524 and a deep part (shown as a right deep part 528 and a left deep part 528' in FIG. 5), see, e.g., *Gray's anatomy: the anatomical basis of medicine and surgery,* 38th ed. (1995). The deep part 528, 528' lies upon the tracheal bifurcation (at the back of the aorta and in front of the tracheal bifurcation) and consists of cardiac branches from all cervical sympathetic ganglia of both right and left sides except the superior left 508', together with superior and inferior cervical and thoracic cardiac branches of the right vagus nerve (parasympathetic) and superior cervical and thoracic branches of the left vagus nerve (parasympathetic).

Figure 6:
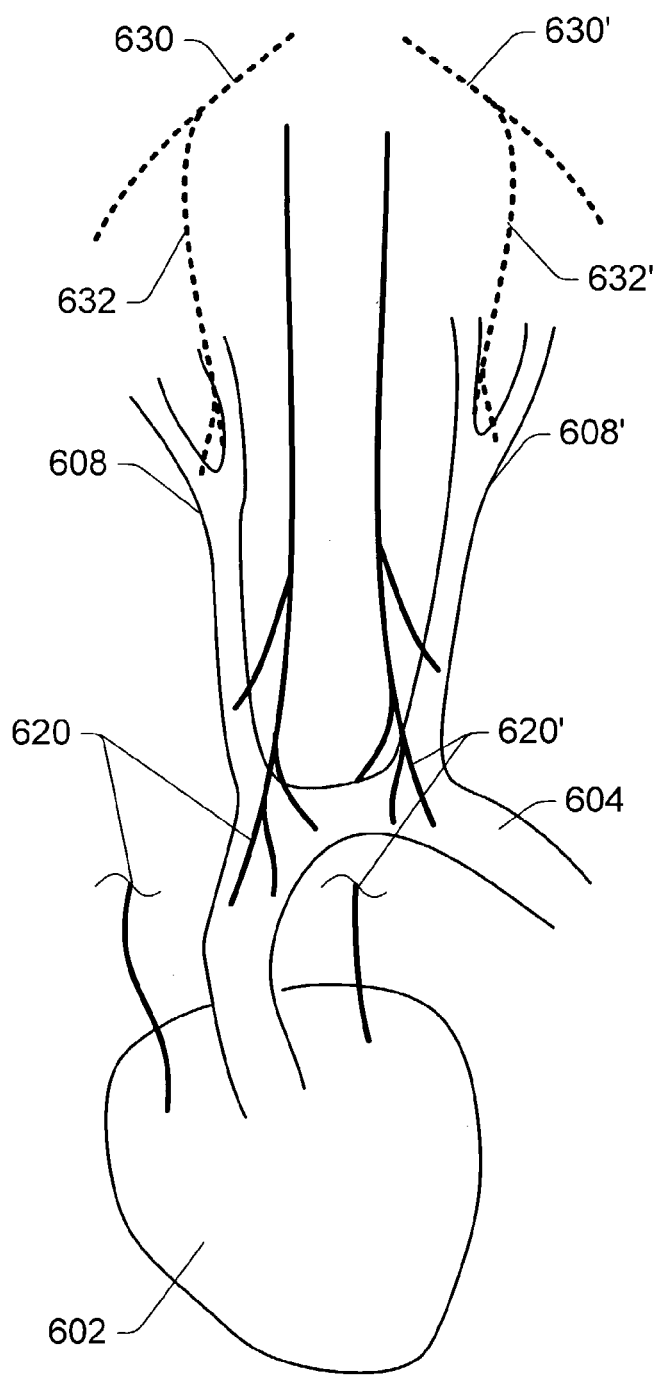
FIG. 6 is a simplified approximate anatomical diagram of parasympathetic afferent pathways.

Referring to FIG. 6, an approximate anatomical diagram of afferent vagal parasympathetic pathways 620, 620' is shown. Vagal afferent pathways include baroreceptors and/or chemoreceptors from the aortic arch 604, carotid arteries 608, 608' and the heart 602. With respect to the heart 602, vagus afferent pathways are known to have receptors associated with atria, ventricles, pulmonary arteries and coronary arteries. Also shown in FIG. 6 are the glossopharyngeal nerves 630, 630' and sinus branches thereof 632, 632'. In general, such afferent pathways lead to the nucleus tractus solitarius in the brainstem. In addition, stimulation of such afferent pathways typically leads to a depressor response. However, a controversial and seemingly undocumented (in humans) reflex known as the "Bainbridge reflex" can increase heart rate due to an increase of the right atrial pressure. In general, cardiac receptors that lead to a neural response are classified as "A" or "B" receptors. B receptors are the predominant stretch receptors and are stimulated by passive stretch of the atria usually during later diastole. B receptors, when stimulated, cause a response similar to baroreceptors, e.g., inhibition of sympathetic nerves and/or excitation of parasympathetic nerves.

Another group of receptors known as left atrial volume receptors respond to increases in transmural pressure: e.g. from increased left atrial volume. Impulses transmitted to the osmoregulatory centers of the hypothalamus result in reduced ADH (antidiuretic hormone, vasopressin) secretion thereby increasing body water loss. Reflex hypotension and bradycardia sometimes follow left atrial distention. With hemorrhage and decreases in left atrial pressure, ADH secretion is increased to induce water retention. Receptors can also cause hormone secretion. For example, mammalian atria have secretory granules containing a small peptide, atrial natriuretic peptide (ANP). ANP is secreted on stretch of the atria. This potent, short lived peptide induces renal secretion of sodium and increase diuresis thus serving to decrease volume. ANP appears to act to decrease CO by decreasing systemic resistance and by increase capillary filtration.

Ventricular, mostly left ventricle, responses include the Bezold-Jarish Reflex, which results from ventricular wall distention stimulating ventricular mechanoreceptors. Such receptors appear to be active only with extreme conditions to protect the ventricle from volume overload (elicit hypotension and bradycardia). The response is a reflex vagal slowing of the heart and simultaneous inhibition of sympathoadrenal activity. The reflex protects against cardiac overstrain, pulmonary edema, and hypovolemia whenever cardiac distention is excessive (e.g., in some CHF patients). The reflex, transmitted by afferent vagal fibers, is thought to exert its sympathetic block via release of endogenous opiods likely acting on the delta-type opiod receptors in the brain.

Epicardial Autonomic Pathways

Pauza et al., "Morphology, distribution, and variability of the epicardiac neural ganglionated subplexuses in the human heart", *The Anatomical Record* 259(4): 353–382 (2000), reported that the epicardial plexus forms seven subplexuses: (I) left coronary, (II) right coronary, (III) ventral right atrial, (IV) ventral left atrial, (V) left dorsal, (VI) middle dorsal, and (VII) dorsal right atrial. Pauza et al., state that, in general, the human right atrium is innervated by two subplexuses (III, VII), the left atrium by three subplexuses (IV, V, VI), the right ventricle by one subplexus (II), and the left ventricle by three subplexuses (I, V, VI). Pauza et al., also note that diagrams from Mizeres, "The cardiac plexus in man", *Am. J. Anat.* 112:141–151 (1963), suggest that "left epicardiac subplexuses may be considered as being formed by nerves derived from the left side of the deep extrinsic cardiac plexus, whereas ventral and dorsal right atrial subplexuses should be considered as being supplied by preganglionated nerves extending from the right vagus nerve and right sympathetic trunk, as their branches course in the adventitia of the right pulmonary artery and superior vena cava". Further, Pauza et al., also state that the left coronary (I), right coronary (II), ventral left atrial (IV) and middle dorsal (VI) subplexuses "may be considered as being formed by the deep extrinsic plexus that receives equally from both vagi and sympathetic trunks". Note that in the Pauza et al., reference, the terms "epicardiac preganglionated nerves" and "epicardiac postganglionated nerves" are differentiated from the meanings of "axons of the preganglionic and postganglionic neurons" that are valid in the nomenclature of the autonomic nervous system, for example, as referred to above with reference to FIG. 3 and FIG. 4. Thus, the term "postganglionic neurons" includes epicardiac/epicardial preganglionic neurons as well as epicardiac/epicardial postganglionic neurons.

Neuroeffectors

Upon stimulation, end terminals (or terminal knobs) of the postganglionic sympathetic nerves (e.g., epicardial postganglionic sympathetic nerves) release norepinephrine, which acts upon the myocardium. Following stimulation and release, norepinephrine remains active for several seconds; norepinephrine may then be reabsorbed by the terminal, diffuse out of the area, or be inactivated by enzymes. The adrenal medulla also secretes norepinephrine (e.g., 75 percent epinephrine and 25 percent norepinephrine) and produces a peripheral effect that typically lasts much longer than that produced by stimulation of the sympathetic postganglionic terminal knobs. While circulating norepinephrine can increase contractility, the effect on normally innervated hearts is relatively minor with respect to norepinephrine released by end terminals. Heart rate, although initially stimulated by norepinephrine, usually decreases over time due to activation of baroreceptors and vagal-mediated (parasympathetic) slowing of the heart rate.

Cardiac tissue membrane receptors, such as alpha receptors and beta receptors, receive chemicals emitted by postganglionic nerves. Alpha receptors are the most common type of sympathetic receptor and they respond strongly to norepinephrine and weakly to epinephrine. Beta receptors are also adrenergic and include beta-1, beta-2 and beta-3 receptors. Cardiac sympathetic receptors are mostly the beta-1 subtype. Beta-1 receptors, which respond approximately equally to norepinephrine and epinephrine, generally act on the myocardium to increase heart rate, contractility, and/or conduction velocity. In contrast, parasympathetic cholinergic muscarinic receptors act on the sinoatrial (SA) node to decrease heart rate and act on the atrioventricular (AV) node to decrease conduction velocity. Adrenergic antagonists (indirect action) include beta-blockers such as proranolol and alpha-blockers such as phentolamine that inhibit receptors. Cholinergic antagonists (indirect action) include alpha-blockers such as atropine.

Electrical and/or Magnetic Stimulation of Autonomic Nerves

Electrical stimulation of autonomic nerves has been reported in the literature, see, e.g., Murakami et al., "Effects of cardiac sympathetic nerve stimulation on the left ventricular end-systolic pressure-volume relationship and plasma norepinephrine dynamics in dogs", *Jpn. Circ. J.* 61(10): 864–71 (1997); and Du et al., "Response to cardiac sympathetic activation in transgenic mice overexpressing beta 2-adrenergic receptor". *Am-J-Physiol*. August; 271(2 Pt 2): H630–6 (1996). Magnetic stimulation of nerves has also been reported, for example, where a nerve is exposed to a time-varying magnetic field, which may induce electrical currents in the nerve.

According to various exemplary methods and/or devices described herein, a series of pulses, or a pulse train, is typically delivered by an implantable stimulation device to stimulate an autonomic nerve, other nerve and/or tissue. The pulse train optionally includes pulse parameters or pulse train parameters, such as, but not limited to, frequency, pulse duration (or pulse width), number of pulses, and/or amplitude. These parameters may have broad ranges and vary over time within any given pulse train. In general, a power level for individual pulses and/or pulse trains is determined based on these parameters and/or other parameters. Exemplary ranges for pulse frequency for nerve and/or tissue stimulation include frequencies ranging from approximately 0.1 to approximately 100 Hz, and, in particular, frequencies ranging from approximately 1 Hz to approximately 20 Hz. Of course, higher frequencies higher than 100 Hz may also be suitable. Exemplary ranges for pulse duration, or pulse width for an individual pulse (generally within a pulse train), include pulse widths ranging from approximately 0.01 milliseconds to approximately 5 milliseconds and, in particular, pulse widths ranging from approximately 0.1 milliseconds to approximately 2 milliseconds. Exemplary pulse amplitudes are typically given in terms of current or voltage; however, a pulse or a pulse trains may also be specified by power, charge and/or energy. For example, in terms of current, exemplary ranges for pulse amplitude include amplitudes ranging from approximately 0.02 mA to approximately 20 mA, in particular, ranging from 0.1 mA to approximately 5 mA. Exemplary ranges for pulse amplitude in terms of voltage include voltages ranging from approximately 1 V to approximately 50 V, in particular, ranging from approximately 1 V to approximately 20 V.

For pulses delivered by implantable stimulation devices having a fixed or otherwise limited power supply, i.e., a power supply having power limitations, average power of a pulse or a pulse train is usually limited acutely by the power capability of the power supply (e.g., battery, fuel cell, nuclear generator, etc.) and chronically by the capacity of the power supply and desired longevity of the device's usefulness. Average power of a pulse is generally given as peak power averaged over one cycle. For example, given a voltage of 10 V, a resistance of 1000 ohms, a pulse frequency of 20 Hz and a pulse width of 1 ms, the peak power is given as voltage squared divided by resistance, which is 0.1 W, and the average power is 20 Hz multiplied by 1 ms multiplied by 0.1 W, which is 0.002 W or 2 mW. The term "power", as used herein, includes, but is not limited to, peak power and average power.

Current drain is another factor often considered when determining power limitations of a power supply. Current drain is generally defined as the average amount of current drawn from a power supply in an implantable pulse generator in one hour. Current drain depends on many factors, including how frequently the device delivers pulses and at what parameters, the circuitry and/or the type of stimulation lead. Current drain is commonly expressed in millionths of an ampere or microamperes. A power drain based on current drain may be determined by the product of current drain and voltage. Such a power is optionally useful in determining a maximum power level for an autonomic stimulation pulse or pulses. Of course, such a power is optionally useful in determining a maximum power level for any stimulation pulse or pulses In general, a maximum power level or maximum power demand for an implantable device may be determined, in part, by the product of the voltage times the current capability of the battery (or other power supply) less circuit inefficiencies. Of course, desired power supply life (e.g., battery life) and/or other factors may be considered. For example, some implantable stimulation devices have a continuous power drain for one function (e.g., to drive a microchip, microprocessor or timing circuitry) and an intermittent function (e.g., such as pacing, measuring, signaling, etc.) which has intermittent power utilization. Consideration of such factors may be necessary in determining a tolerable and/or maximum power level and, in particular, in determining pulse parameters.

Vessels and Stimulation of Autonomic Nerves, Other Nerves and/or Tissue

According to various exemplary methods and stimulation devices described herein, and equivalents thereof, stimulation of parasympathetic nerves, other nerves and/or tissue allows for influence of cardiac activity. For example, various exemplary methods and corresponding stimulation devices rely on placement of one or more electrodes in a vessel, e.g., an epicardial vein or an epicardial venous structure. Suitable epicardial veins or venous structures include the coronary sinus and veins that drain into the coronary sinus, either directly or indirectly. For example, the great cardiac vein passes along the interventricular sulcus, with the anterior interventricular coronary artery, and empties anteriorly into the coronary sinus; and the middle cardiac vein travels with the posterior (right) interventricular coronary artery and empties into the coronary sinus posteriorly. Other suitable veins include those that drain into the right atrium or right auricle. For example, the anterior cardiac vein passes through the wall of the right atrium and empties into the right atrium.

Other exemplary methods and/or devices rely on placement of one or more electrodes in a non-epicardial vein. Such exemplary methods and/or devices are optionally suitable for stimulation of parasympathetic nerves at locations, for example, generally along a parasympathetic pathway between the heart and brain. Further, other exemplary methods and/or devices rely on placing one or more electrodes through the wall of a vein and proximate to a parasympathetic nerve, other nerve and/or tissue.

Figure 7:
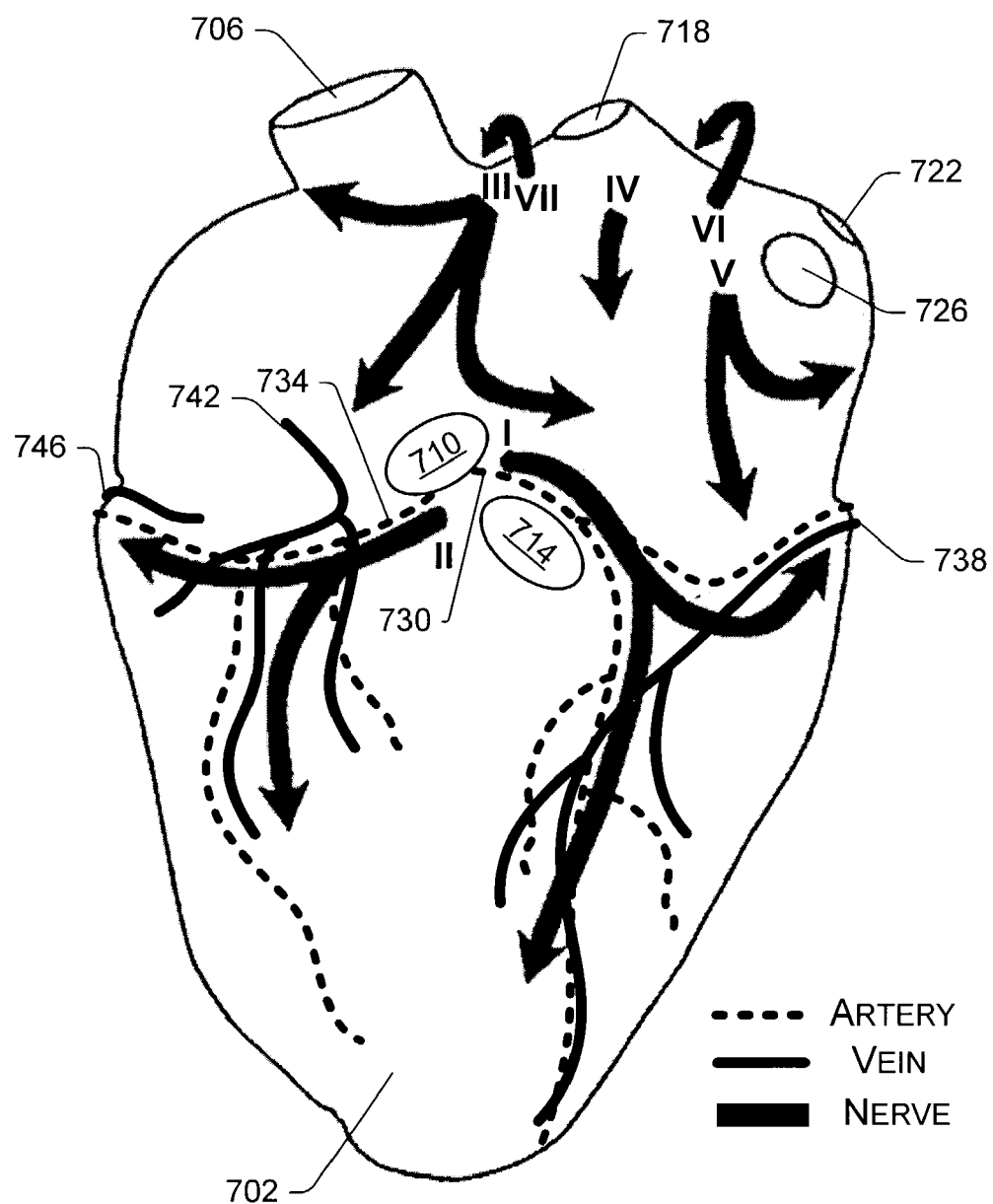
FIG. 7 is an approximate anatomical ventral view diagram of a human heart including some arteries, veins and nerves.

Referring to FIG. 7, a ventral diagram of a human heart 702 is shown. Various anatomical features of the heart 702 are also shown and include an opening to the superior vena cava 706, an opening to the aorta 710, an opening to the pulmonary trunk 714, an opening to the right superior pulmonary vein 718, an opening to the left inferior pulmonary vein 722, and an opening to the left superior pulmonary vein 726. FIG. 7 also shows some of the epicardial arteries (thick dashed lines) and veins (thick solid lines). Under normal conditions, epicardial arteries carry oxygenated blood to the myocardium, primarily myocardium of the ventricles while epicardial veins carry blood deoxygenated by the myocardium to the right atrium of heart 702. Pressure in the veins is generally, on average, much less than pressure in the arteries.

Two major epicardial arterial networks are shown in FIG. 7 and associated with the left coronary artery 730 and the right coronary artery 734. The left coronary artery 730 stems from the aorta near the opening to the aorta 710 and travels along the base of the left ventricle where it branches. One branch of the left coronary artery travels on the epicardial surface of the left ventricle toward the apex of the heart 702 (known as the left anterior descending artery) while another branch travels on the epicardial surface of the left ventricle toward the dorsal side of the heart 702 (known as the circumflex branch of the left coronary artery). The right coronary artery 734 stems from the aorta near the opening to the aorta 710 and travels along the base of the right ventricle where it branches. Various branches of the right coronary artery 734 travel on the epicardial surface of the right ventricle while at least one branch travels on the epicardial surface of the right ventricle toward the dorsal side of the heart 702.

Three major epicardial venous networks are shown in FIG. 7, which are associated with the great cardiac vein 738, the anterior cardiac vein 742, and the small cardiac vein 746. The great cardiac vein 738 receives blood from a network that spreads across the ventral side of the epicardial surface of the left ventricle and major branches of the network extend toward the apex of the heart 702. As already mentioned, the great cardiac vein 738 travels on the epicardial surface near the base of the left ventricle to the dorsal side of the heart 702 where it joins the coronary sinus vein. The anterior cardiac vein 742 receives blood from a network that spreads across the ventral and dorsal sides of the epicardial surface of the right ventricle and major branches of the network extend toward the apex of the heart 702. As already mentioned, the anterior cardiac vein empties into the right atrium of the heart 702. The small cardiac vein 746 travels from the ventral epicardial surface to the dorsal epicardial surface where it empties into the coronary sinus.

FIG. 7 also shows the seven subplexuses as identified by Pauza et al. Preganglionate nerves enter the left coronary subplexus (I) and the right coronary subplexus (II) approximately between the opening to the aorta 710 and the opening to the pulmonary trunk 714. Preganglionate nerves enter the ventral right atrial subplexus (III) at the superior interatrial sulcus and non-regularly on the ventral surface of the root of the superior vena cava while preganglionated nerves enter the ventral left atrial subplexus (IV) approximately between the superior interatrial sulcus and left atrial nerve fold. Preganglionated nerves enter the left dorsal subplexus (V) approximately at the left atrial nerve fold and preganglionated nerves enter the middle dorsal subplexus (VI) approximately between the right and left superior pulmonary veins (see, e.g., 718, 726) and, non-regularly, between the right pulmonary veins and the inferior vena cava. Preganglionated nerves enter the dorsal right atrial subplexus (VII) approximately between the superior vena cava and the right superior pulmonary vein (see, e.g., 706, 718). As already mentioned, postganglionated nerves, and some preganglionated nerves, spread out from the subplexuses (I–VII) across the epicardial surface of the heart 702. The spreading of such nerves is shown by the thick solid arrows in FIG. 7 and FIG. 8, the latter of which shows a dorsal diagram of the heart 702.

Figure 8:
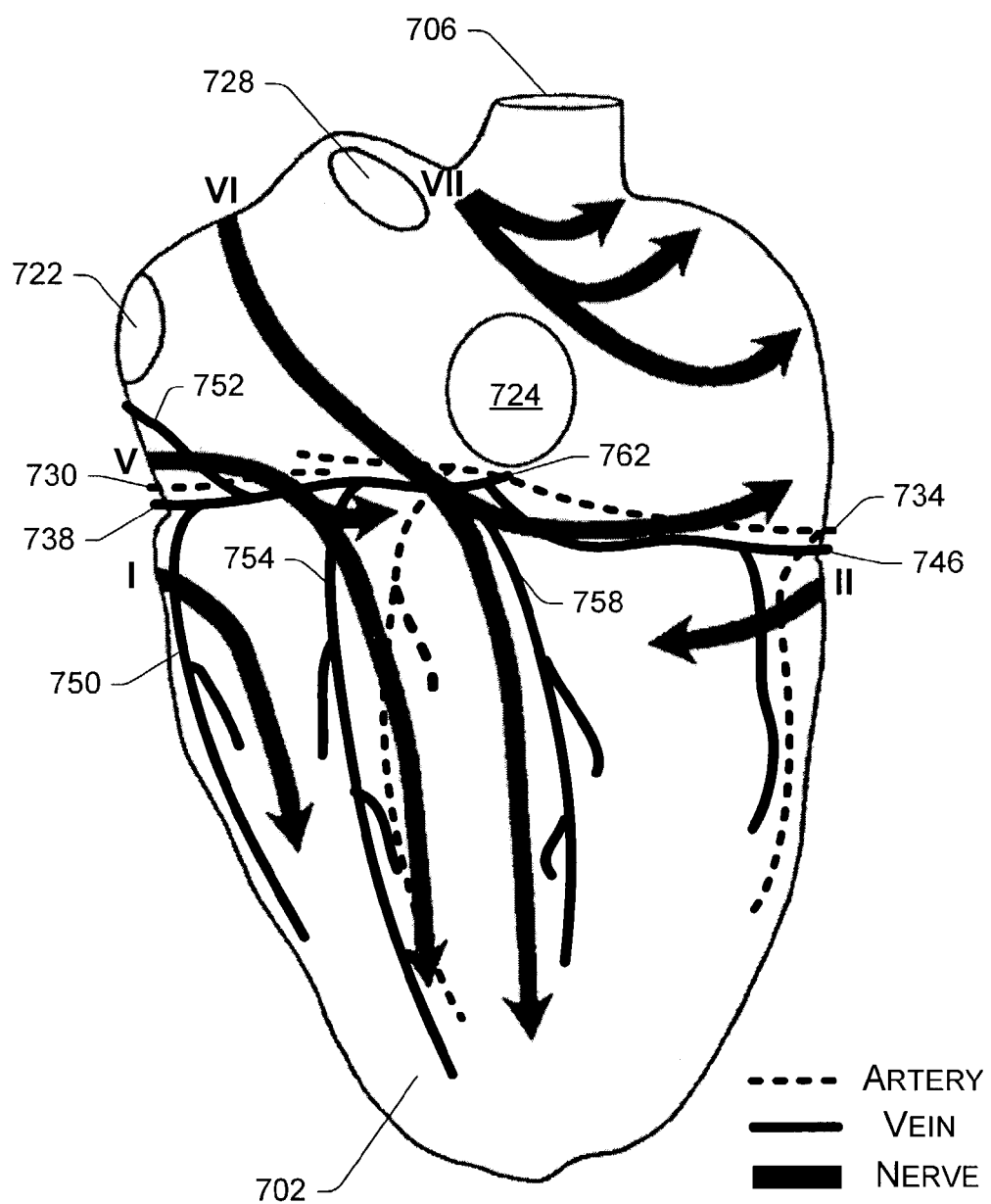
FIG. 8 is an approximate anatomical dorsal view diagram of a human heart including some arteries, veins and nerves.

Referring to FIG. 8, a dorsal diagram of the human heart 702 is shown. Various anatomical features of the heart 702 are also shown and include an opening to the superior vena cava 706, an opening to the inferior vena cava 724, an opening to the right inferior pulmonary vein 728, and an opening to the left inferior pulmonary vein 722. FIG. 8 also shows some of the epicardial arteries (thick dashed lines) and veins (thick solid lines). The arterial and venous networks shown on the dorsal epicardial surface of the heart 702 include extensions of networks from the ventral epicardial surface. For example, the dorsal epicardial surface includes networks stemming the right coronary artery 734 and the left coronary artery 730. In particular, the circumflex branch of the left coronary artery 730 is shown along with various extensions of the right coronary artery 734 one of which approaches the end of the circumflex branch. Venous epicardial structures shown in FIG. 8 include the coronary sinus 762, the great cardiac vein 738, the small cardiac vein 746, the oblique vein of the left atrium 752, the left marginal vein 750, the posterior vein of the left ventricle 754, and the middle cardiac vein 758. The aforementioned veins (738, 746, 750, 752, 754, 758) empty into the coronary sinus 762.

FIG. 7 also shows, via thick solid arrows, neural extensions of five of the subplexuses as identified by Pauza et al. Neural extensions of the left coronary subplexus (I) descend toward the apex of the heart 702 at and/or near the left marginal vein 750 and the posterior vein of the left ventricle 754. Neural extensions of the right coronary subplexus (II) traverse the heart 702 at and/or near the right coronary sulcus. Neural extensions of the left dorsal subplexus (V) descend toward the apex of the heart 702 at and/or near the posterior vein of the left ventricle 754 while neural extensions of the middle dorsal subplexus (VI) descend towards the apex of the heart 702 at and/or near the middle cardiac vein 758 and the small cardiac vein 746. Neural extensions of the dorsal right atrial subplexus (VII) extend around the right atrium at and/or near the superior vena cava (see, e.g., 706) and the inferior vena cava (see, e.g., 724).

As shown in FIGS. 7 and 8, various epicardial veins or venous structures travel at and/or near epicardial subplexuses and/or epicardial extensions of epicardial subplexuses. According to various exemplary methods and/or stimulation devices described herein, at least one electrode is placed in the lumen of an epicardial vein or venous structure and/or through the wall of an epicardial vein or venous structure. Further, upon passing current through the at least one electrode, neural and/or tissue stimulation occurs, which may cause release of a neuroeffector, such as, but not limited to, acetylcholine.

Stimulation of Nerves and/or Tissue for Arrhythmia Discrimination

Various exemplary methods described herein deliver one or more stimulation pulses to alter conduction and/or operation of the AV node and/or the AV bundle to aid in classification of cardiac activity, such as, but not limited to, ventricular arrhythmia. In addition, various exemplary methods optionally increase stimulation pulse power and/or change stimulation site wherein multiple stimulation pulses are delivered.

Figure 9:
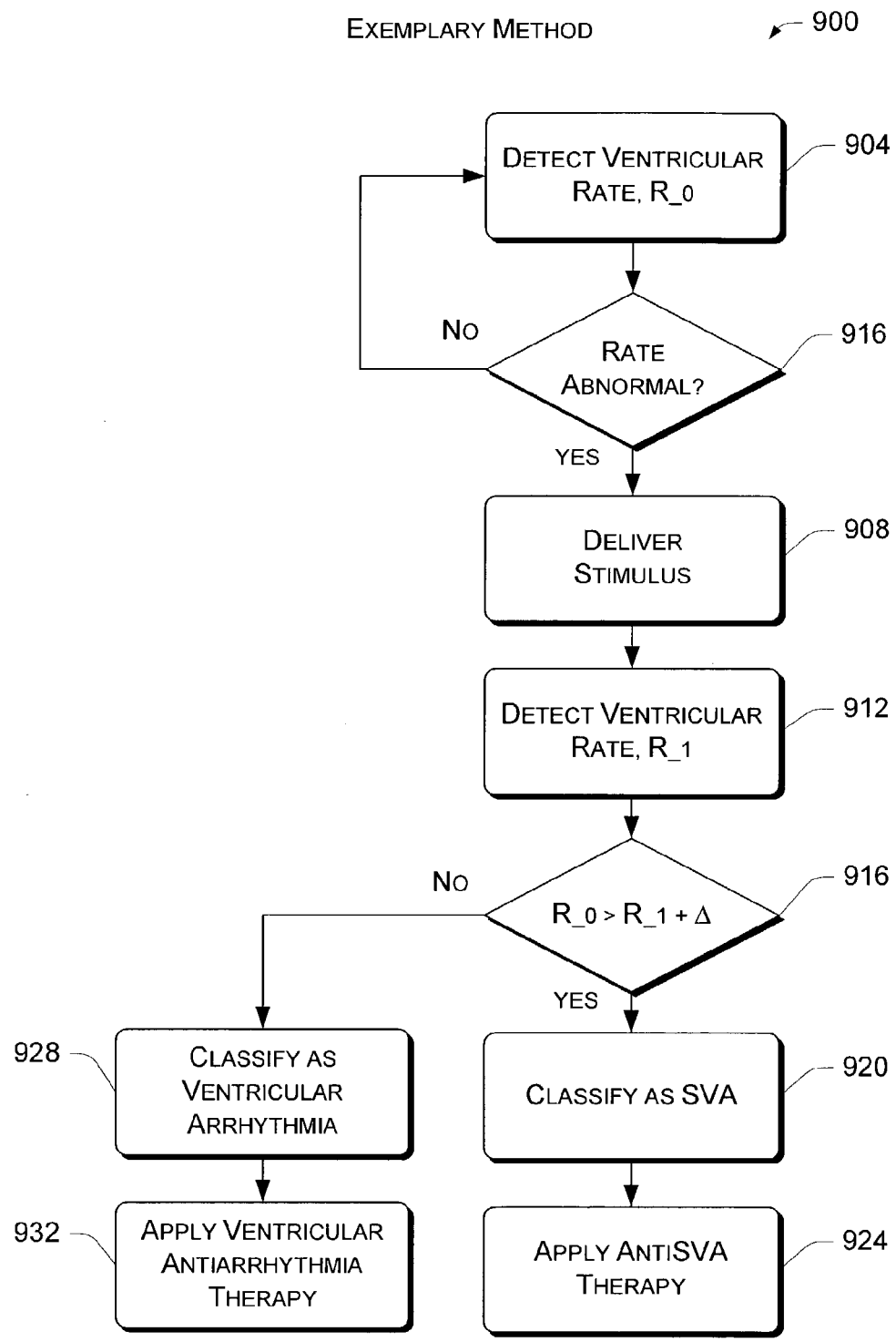
FIG. 9 is a block diagram of an exemplary method for stimulating a nerve and/or tissue to alter conduction and/or operation of a patient's AV node and/or AV bundle and to classify an arrhythmia.

Referring to FIG. 9, an exemplary method 900 for classifying cardiac activity is shown. In a detection block 904, an implantable stimulation device detects a ventricular rate R_0. Next, in a decision block 916, the implantable stimulation device determines whether the ventricular rate R_0 is abnormal, for example, faster than normal by some percentage (e.g., 120% of normal or more, etc.). Such an exemplary determination may account for an otherwise normally elevated rate, for example, due to an exercise state wherein monitoring optionally persists but no substantive action is taken. If the decision block 916 indicates that the ventricular rate R_0 is abnormal, then, in a delivery block 908, the stimulation device delivers one or more stimulation pulses to alter conduction and/or operation of the AV node and/or the AV bundle. As described above, stimulation of various nerves and/or tissue may slow conduction of action potentials through the AV node and/or the AV bundle. Thus, action potentials originating from supraventricular arrhythmias are likely to have less effect on ventricular rate if the AV node and/or the AV bundle slow conduction of such action potentials. After the delivery, in another detection block 912, the stimulation detects another ventricular rate $R\_1$. A logic block 916 follows wherein the stimulation device determines whether the ventricular rate $R\_0$ is greater than the ventricular rate $R\_1$ plus some value $\Delta$, which is optionally zero. If the logic block 916 indicates that the ventricular rate $R\_0$ is greater than the ventricular rate $R\_1$ plus $\Delta$, then, in a classification block 920, the stimulation device classifies the ventricular rate $R\_0$ as a rate characteristic of a supraventricular arrhythmia. However, if the logic block 916 indicates that the ventricular rate $R\_0$ is not greater than the ventricular rate $R\_1$ plus $\Delta$, then, in another classification block 928, the stimulation device classifies the ventricular rate $R\_0$ as a rate characteristic of a ventricular arrhythmia. Respective application blocks 924, 932 follow the classification blocks 920, 928, wherein the stimulation device optionally implements a suitable antiarrhythmia therapy.

Figure 10:
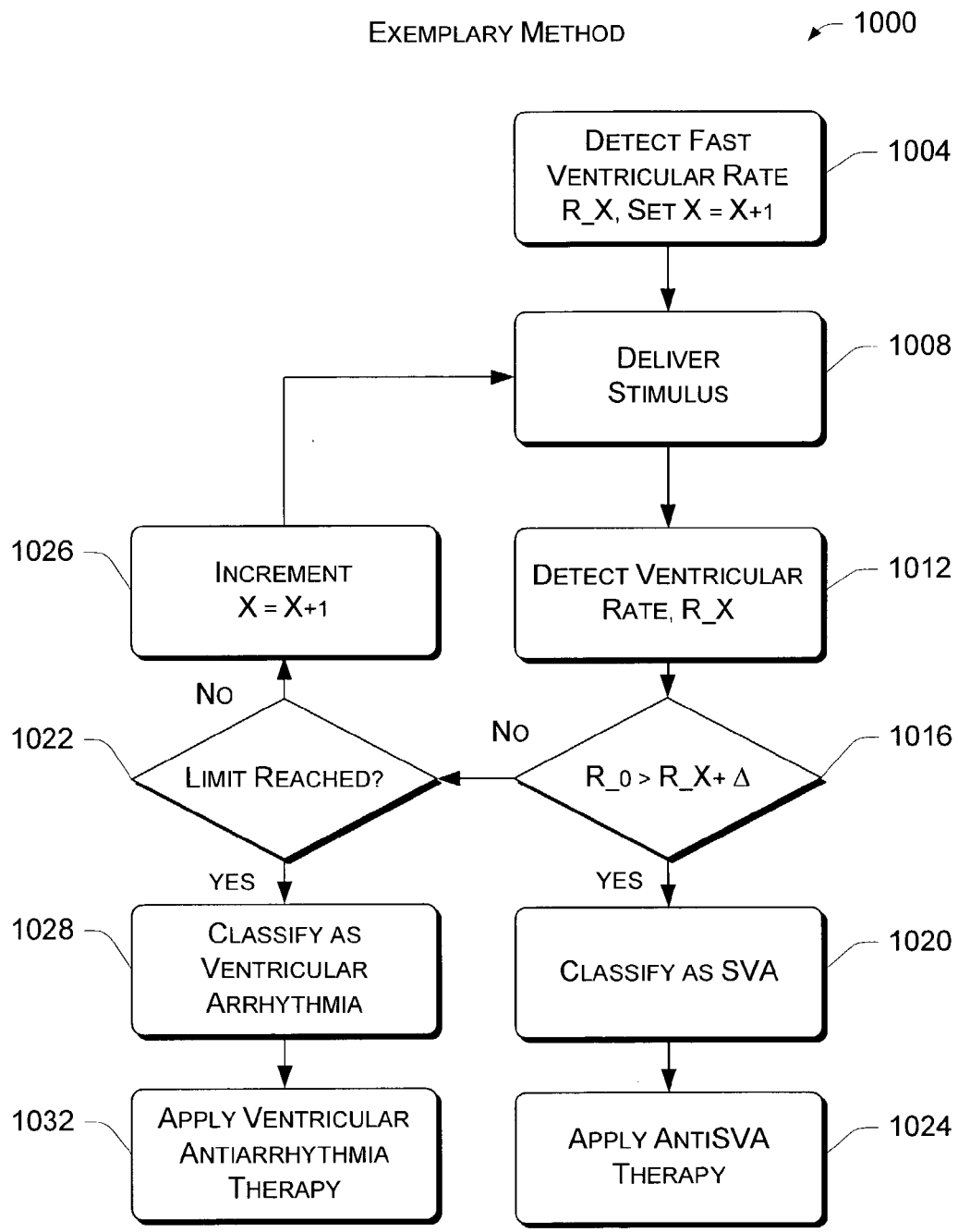
FIG. 10 is a block diagram of an exemplary method for stimulating a nerve and/or tissue one or more times to alter conduction and/or operation of a patient's AV node and/or AV bundle and to classify an arrhythmia.

Referring to FIG. 10, another exemplary method 1000 for classifying cardiac activity is shown. In a detection block 1004, an implantable stimulation device detects a fast ventricular rate, $R\_0$. Upon detection of the fast ventricular rate, the detection block 1004 increments a counter X (e.g., X=X+1). Next, in a delivery block 1008, the implantable stimulation device delivers a stimulus to a nerve and/or other tissue to alter conduction and/or operation of the AV node and/or the AV bundle to thereby induce some degree of AV block. For example, an exemplary implantable stimulation device may deliver a pulse or pulse train having pulse width(s) of approximately 10 microseconds to approximately 500 microseconds, a frequency of approximately 2 Hz to approximately 100 Hz, and/or a duty cycle of approximately 10% or less.

Immediately thereafter, or alternatively after a suitable delay, the implantable stimulation device detects, in another detection block 1012, a post-stimulus ventricular rate $R\_X$. A logic block 1016 follows wherein the stimulation device uses logic to determine whether the rate $R\_0$ exceeds the rate $R\_X$ plus a value $\Delta$ (e.g., where $\Delta$ is optionally zero, a percentage of $R\_0$, etc.). If the rate $R\_0$ exceeds the rate $R\_X$ plus $\Delta$, then, in a classification block 1020, the arrhythmia is classified as a SVA. Following classification, in an application block 1024, the implantable stimulation device optionally applies antiSVA therapy.

However, if the logic block 1016 determines that the rate $R\_0$ is less than or equal to the rate $R\_X$ plus $\Delta$, then, in a decision block 1022, the implantable stimulation device determines whether a cycle limit has been reached. For example, if X is initially 0 and set to 1 in the detection block 1004, then a cycle limit may be set at approximately 2 cycles to approximately 20 cycles. In general, a classification method should not cause too long a delay before implementation of a ventricular antiarrhythmia therapy. For example, in the case of a severe ventricular arrhythmia, antiarrhythmia therapy should be applied typically within a minute (e.g., 60 seconds or less) or at most within a few minutes of onset (e.g., 180 seconds or less). Again, if a reduction in ventricular rate does not occur after repeated induction of block, then the elevated ventricular rate usually originates in and/or near the ventricles and does not depend on conduction via the AV node or nodal area. Further, while a cycle length of 1 cycle may prove effective, caution is typically exercised before delivering a cardioversion or defibrillation shock. Thus, cycle length is optionally adjusted to meet a patient's needs (e.g., health, risk of ventricular arrhythmia, tolerance to pain, shock level, etc.).

Referring again to FIG. 10, if the decision block 1022 indicates that the cycle length is not reached, then the counter X is incremented in an increment block 1026 and the exemplary method 1000 continues at the delivery block 1008. However, if the cycle limit is reached, which indicates that stimulation did not adequately slow the ventricular rate, then, in a classification block 1028, the arrhythmia is classified as a ventricular arrhythmia. Following classification, in an application block 1032, the implantable stimulation device optionally applies antiarrhythmia therapy (e.g., antitachycardia pacing, cardioversion stimulus, and/or defibrillation stimulus).

While the exemplary method 1000 of FIG. 10 implements relatively simply logic in the logic block 1016, an alternative exemplary method implements more advanced logic. For example, more advanced logic optionally includes averaging, derivative and/or integral algorithms. Derivative algorithms include, but are not limited to, slope and/or curvature algorithms that assess changes in rate with respect to time. Algorithms that average rates optionally include forgetting factors to weigh one or more rates.

Figure 11:
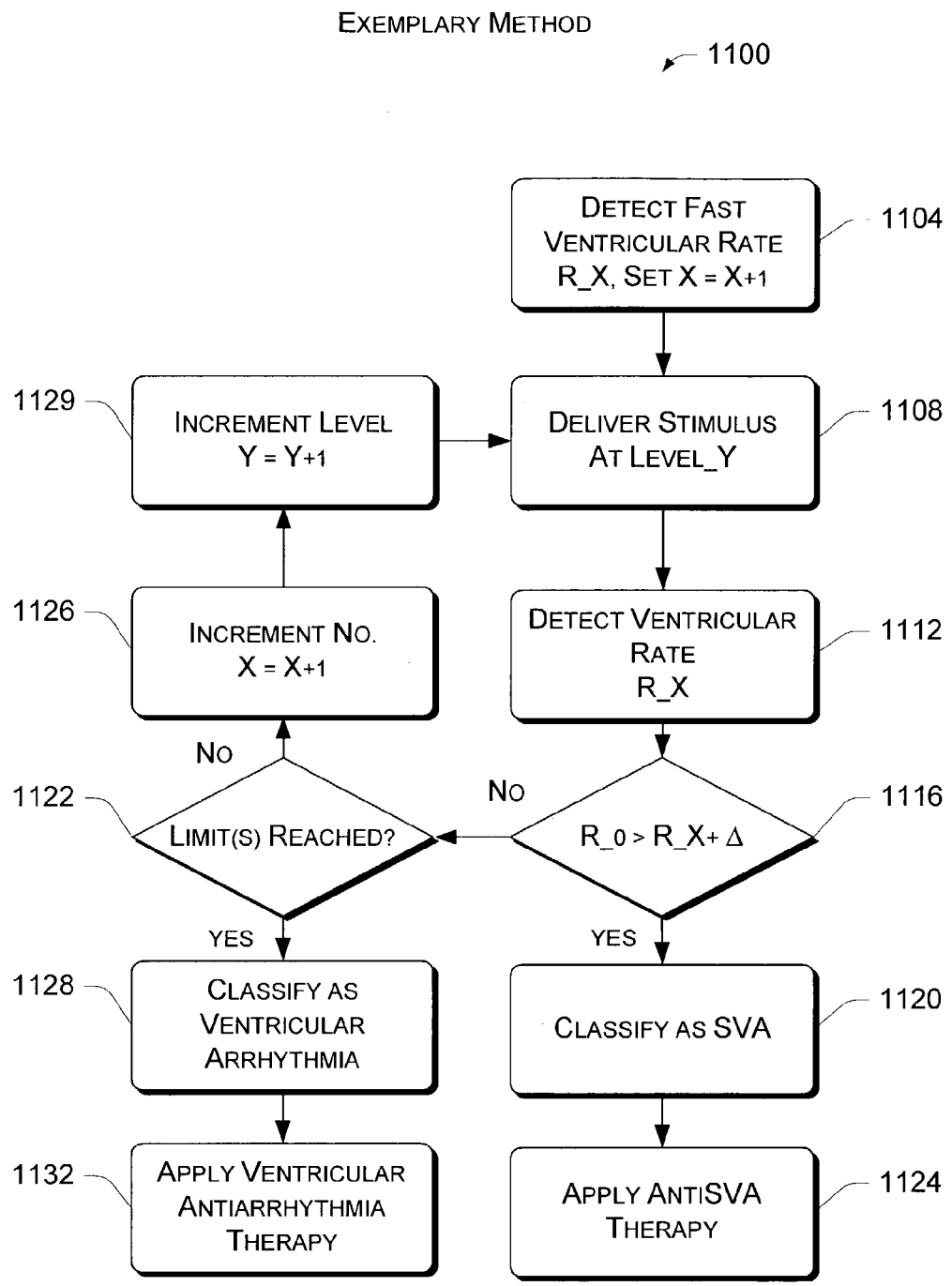
FIG. 11 is a block diagram of an exemplary method for stimulating a nerve and/or tissue one or more times at one or more power levels to alter conduction and/or operation of a patient's AV node and/or AV bundle and to classify an arrhythmia.

Referring to FIG. 11, a block diagram of an exemplary method 1100 is shown. The exemplary method 1100 includes many features of the exemplary method 1000 of FIG. 10; however, the delivery block 1108 of the exemplary method 1100 allows for delivery of stimulation pulses at one or more levels. As described below, such a method may conserve power and/or allow for more expeditious reversibility of the AV node and/or AV bundle.

Referring to FIG. 11, in a detection block 1104, an implantable stimulation device detects a fast ventricular rate $R\_0$. Upon detection of the fast ventricular rate, the detection block 1104 increments a counter X (e.g., X=X+1). Next, in a delivery block 1108, the implantable stimulation device delivers a stimulus at a level (e.g., Level Y) to a nerve and/or other tissue to thereby induce some degree of AV block. For example, Level_0 (wherein Y equals 0) may correspond to one pulse or pulse train whereas Level_1 (wherein Y equals 1) may correspond to another pulse or pulse train. Thus, the value of Y is optionally an integer corresponding to different stimulation parameters, such as, but not limited to, pulse width, frequency, amplitude, duty cycle, etc.

Immediately after the delivery block 1108, or alternatively after a suitable delay, the implantable stimulation device, in another detection block 1112, detects the ventricular rate, $R\_X$. In a logic block 1116 follows wherein the stimulation device uses logic to determine whether the rate $R\_0$ exceeds the rate $R\_X$ plus a value $\Delta$ (e.g., where $\Delta$ is optionally zero, a percentage of $R\_0$, etc.). If the stimulation device determines that the rate $R\_0$ exceeds the rate $R\_X$ plus $\Delta$, then, in a classification block 1120, the fast ventricular rate is classified as characteristic of a SVA. Following classification, in an application block 1124, the implantable stimulation device optionally applies antiSVA therapy.

However, if the logic block 1116 determines that the rate $R\_0$ is less than or equal to the rate $R\_X$ plus A, then, in a decision block 1122, the implantable stimulation device determines whether a cycle limit or another stimulus related limit has been reached. For example, if X is initially 0 and set to 1 in the detection block 1104, then a cycle limit may be set at approximately 2 cycles to approximately 10 cycles. In general, a classification method should not cause too long a delay before implementation of a ventricular antiarrhythmia therapy. For example, in the case of a severe ventricular arrhythmia, antiarrhythmia therapy should be applied typically within a minute (e.g., approximately 60 seconds or less) or at most within a few minutes of onset (e.g., approximately 180 seconds or less). Again, if a reduction in ventricular rate does not occur after repeated induction of block, then the elevated ventricular rate usually originates in and/or near the ventricles and does not depend on conduction via the AV node or nodal area. Further, while a cycle length of 1 cycle may prove effective, caution is typically exercised before delivering a cardioversion or defibrillation shock. Thus, cycle length is optionally adjusted to meet a patient's needs (e.g., health, risk of ventricular arrhythmia, tolerance to pain, shock level, etc.).

As already mentioned, the decision block 1122 optionally decides whether another stimulus related limit has been reached, such as, but not limited to, stimulation pulse width, stimulation pulse frequency, stimulation pulse duty cycle, stimulation pulse amplitude, etc. For example, to conserve energy, to reduce risk of irreversible block, and/or to promote recovery after induction of some degree of block, the delivery block 1108 delivers a stimulus at a low power (e.g., wherein Level_0 corresponds to a low power level). According to this example, the power level is optionally increased as Y is incremented (e.g., via increment block 1129) from 0 to 1, etc. (e.g., Level_1 optionally equals 110% of Level_0, etc.). Of course, stimulus level is optionally adjusted to meet a patient's needs (e.g., health, risk of ventricular arrhythmia, tolerance to pain, shock level, etc.).

In such an exemplary method 1100, at some point, either a cycle limit and/or another stimulus related limit will be reached. In the instance that a maximum stimulation power level is reached per the decision block 1122, while the check block 1116 indicates that an insufficient reduction in rate, then the exemplary method 1100 continues at a classification block 1128, wherein the fast ventricular rate is classified as characteristic of a ventricular arrhythmia. Following classification, in an application block 1132, the implantable stimulation device optionally applies antiarrhythmia therapy (e.g., antitachycardia pacing, cardioversion stimulus, and/or defibrillation stimulus).

While the exemplary method 1100 of FIG. 11 implements relatively simply logic in the logic block 1116, an alternative exemplary method implements more advanced logic. For example, more advanced logic optionally includes averaging, derivative and/or integral algorithms. Derivative algorithms include, but are not limited to, slope and/or curvature algorithms that assess changes in rate with respect to time. Algorithms that average rates optionally include forgetting factors to weigh one or more rates. Further, such more advanced logic optionally accounts for stimulation level delivered in the delivery block 1108.

Figure 12:
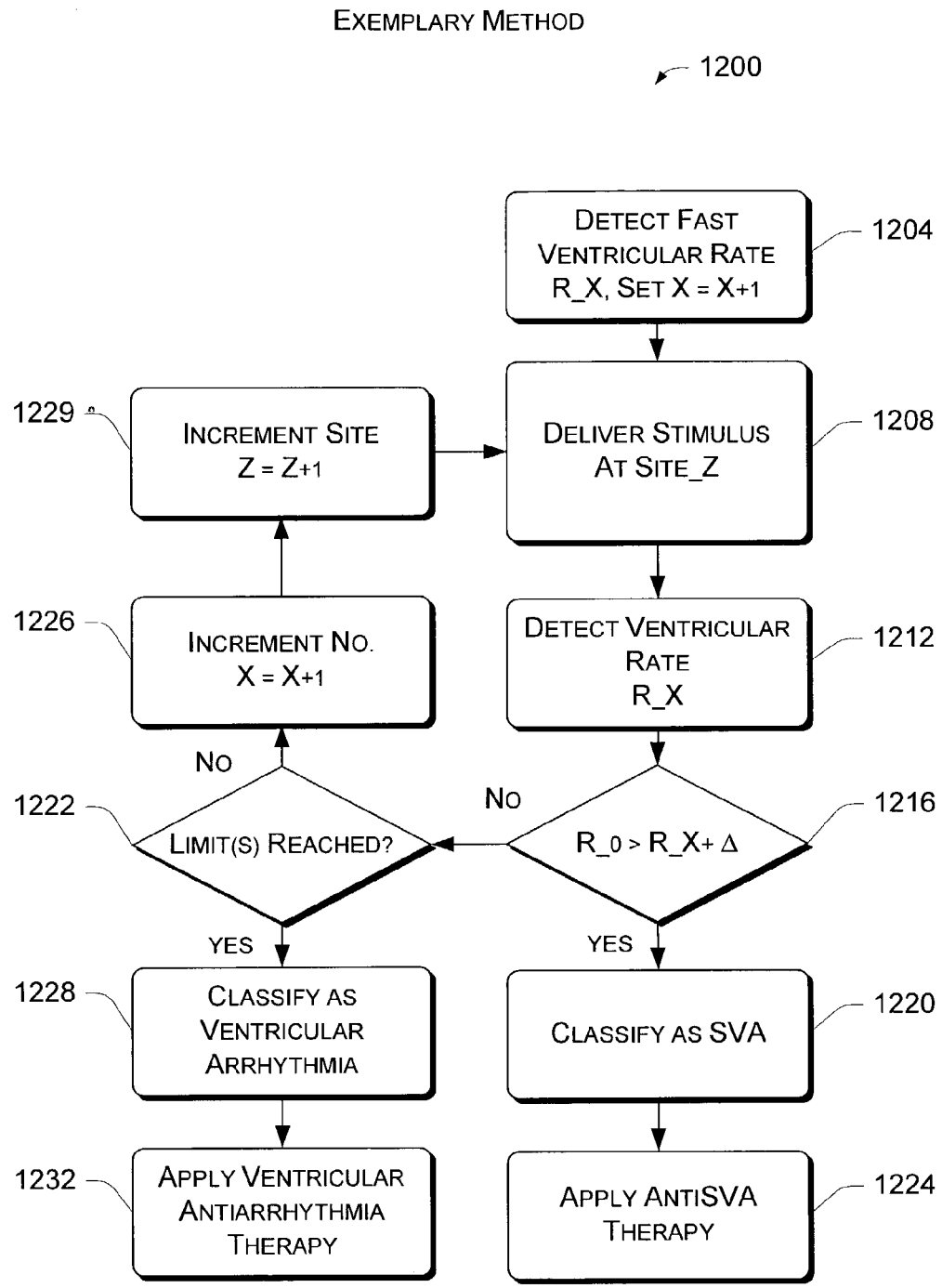
FIG. 12 is a block diagram of an exemplary method for stimulating a nerve and/or tissue one or more times at one or more sites to alter conduction and/or operation of a patient's AV node and/or AV bundle and to classify an arrhythmia.

Referring to FIG. 12, a block diagram of an exemplary method 1200 is shown. The exemplary method 1200 includes many features of the exemplary method 1000 of FIG. 10 and of the exemplary method 1100 of FIG. 11; however, the delivery block 1208 of the exemplary method 1200 allows for delivery of stimulation pulses at one or more sites. According to such an exemplary method, for any given condition, stimulation at one site may alter conduction and/or operation of the AV node and/or AV bundle more favorably than stimulation at another site. Thus, a stimulation device may optionally stimulate at one site, detect cardiac activity and then stimulate at another site if no significant change in cardiac activity was found.

Referring to FIG. 12, in a detection block 1204, an implantable stimulation and/or other device detects a fast ventricular rate, R_0. Upon detection of the fast ventricular rate, the detection block 1204 increments a counter X (e.g., X=X+1). Next, in a delivery block 1208, the implantable stimulation device delivers a stimulus at a certain site (e.g., Site_Z) to a nerve and/or other tissue to alter conduction and/or operation of the AV node and/or the AV bundle to thereby slow conduction (e.g., induce some degree of AV block). For example, an exemplary implantable stimulation device may deliver a pulse or pulse train at Site_Z, where Z is optionally an integer corresponding to different stimulation sites, such as, but not limited to, epicardial sites, endocardial sites, etc.

Immediately after the delivery block 1208, or alternatively after a suitable delay, the implantable stimulation device detects, in another detection block 1212, the ventricular rate R_X. A logic block 1216 follows wherein the stimulation device uses logic to determine whether the rate R_0 exceeds the rate R_X plus a value Δ (e.g., where Δ is optionally zero, a percentage of R_0, etc.). If the logic block 1216 indicates that the rate R_0 exceeds the rate R_X plus Δ, then, in a classification block 1120, the fast ventricular rate is classified as characteristic of a SVA. Following classification, in an application block 1224, the implantable stimulation device optionally applies antiSVA therapy.

However, if the logic block 1216 determines that the rate R_0 is less than or equal to the rate R_X plus Δ, then, in a decision block 1222, the implantable stimulation device determines whether a cycle limit or another stimulus related limit has been reached. For example, if X is initially 0 and set to 1 in the detection block 1204, then a cycle limit may be set at approximately 2 cycles to approximately 10 cycles. In general, a classification method should not cause too long a delay before implementation of a ventricular antiarrhythmia therapy. For example, in the case of a severe ventricular arrhythmia, antiarrhythmia therapy should be applied typically within a minute (e.g., approximately 60 seconds or less) or at most within a few minutes of onset (e.g. approximately 180 seconds or less). Again, if a reduction in ventricular rate does not occur after repeated induction of block, then the elevated ventricular rate usually originates in and/or near the ventricles and does not depend on conduction via the AV node or nodal area. While a cycle length of 1 cycle may prove effective, caution is typically exercised before delivering a cardioversion or defibrillation shock. Thus, cycle length is optionally adjusted to meet a patient's needs (e.g., health, risk of ventricular arrhythmia, tolerance to pain, shock level, etc.).

As already mentioned, the decision block 1222 optionally decides whether another stimulus related limit has been reached, such as, but not limited to, a site limit. For example, on the basis of experience and/or design, various stimulation sites may exhibit differing characteristics that pertain to induction of AV block. Thus, according to this example, a first site is optionally chosen wherein the first site corresponds to a higher probability of AV block induction. Further, sites are optionally characterized by stimulus energy needed to induce some degree of AV block. If a particular site (or sites) does not result in a reduction in ventricular rate, then Z is incremented (e.g., via increment block 1229) from 0 to 1, etc. (e.g., wherein Site_0 differs from Site_1). Of course, a stimulus site or sites are optionally chosen to meet a patient's needs (e.g., health, risk of ventricular arrhythmia, tolerance to pain, shock level, etc.).

In such an exemplary method 1200, at some point, either a cycle limit and/or another stimulus related limit will be reached. In the instance that none of the sites adequately reduce ventricular rate, as indicated by a correspond limit (e.g., progression through three of three sites), while the logic block 1216 indicates that an insufficient reduction in rate, then the exemplary method 1200 continues at a classification block 1228, wherein the fast ventricular rate is classified as characteristic of a ventricular arrhythmia. Following classification, in an application block 1232, the implantable stimulation device optionally applies antiarrhythmia therapy (e.g., antitachycardia pacing, cardioversion stimulus, and/or defibrillation stimulus).

While the exemplary method 1200 of FIG. 12 implements relatively simply logic in the logic block 1216, an alternative exemplary method implements more advanced logic. For example, more advanced logic optionally includes averaging, derivative and/or integral algorithms. Derivative algorithms include, but are not limited to, slope and/or curvature algorithms that assess changes in rate with respect to time. Algorithms that average rates optionally include forgetting factors to weigh one or more rates. Further, such more advanced logic optionally accounts for parasympathetic stimulation site characteristics based on the site or sites stimulated in the delivery block 1208.

Figure 13:
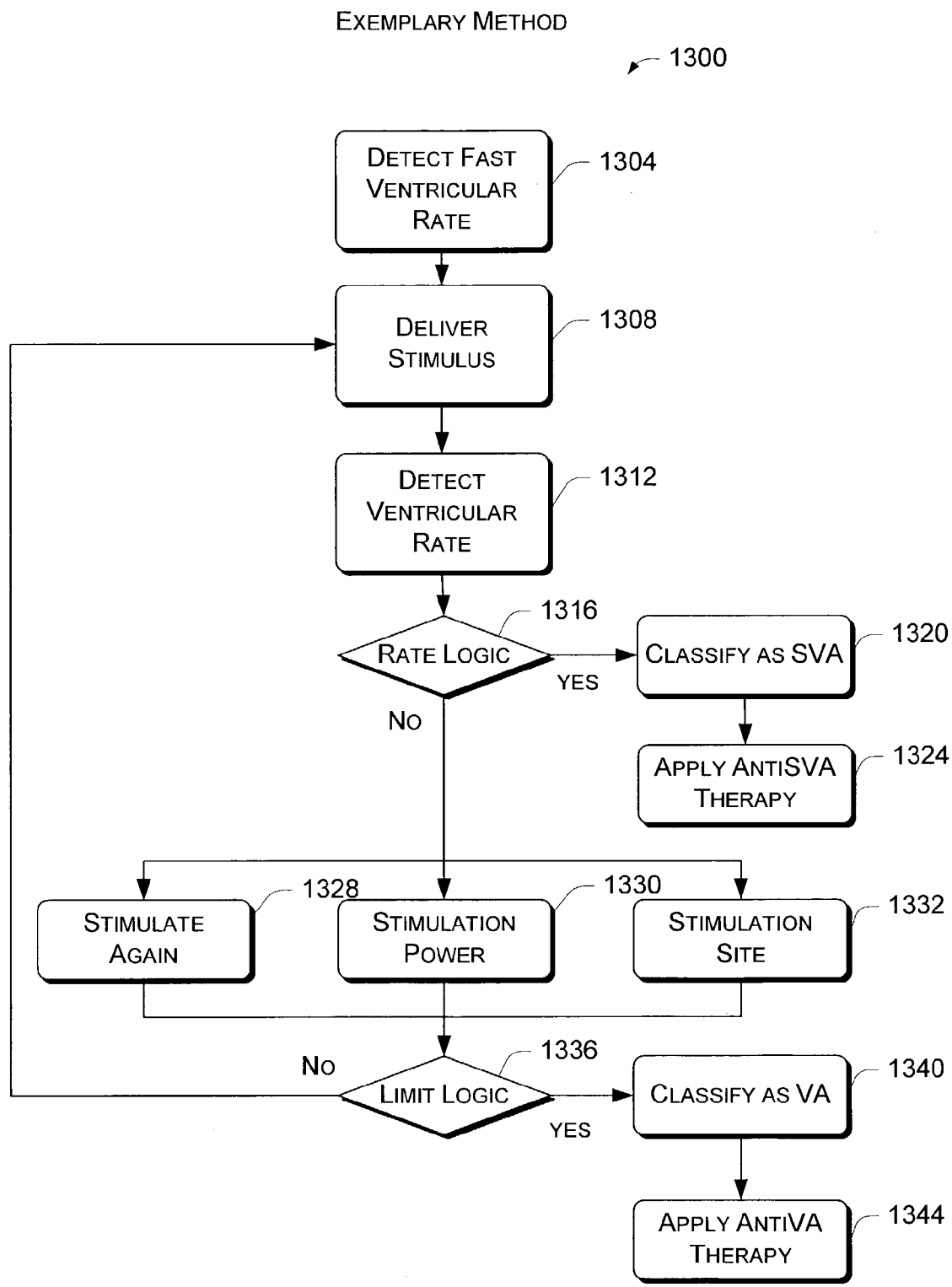
FIG. 13 is a block diagram of an exemplary method for stimulating a nerve and/or tissue one or more times at one or more power levels and/or at one or more sites to alter conduction and/or operation of a patient's AV node and/or AV bundle and to classify an arrhythmia.

Referring to FIG. 13, a block diagram of an exemplary method 1300 is shown. The exemplary method 1300 optionally includes features of the exemplary methods 1000, 1100, and/or 1210. Referring to FIG. 13, the exemplary method 1300 involves delivering a stimulation pulse to the one or more electrodes at a particular site (or sites) to thereby stimulate one or more nerves and/or other tissue which, in turn, induce may induce some degree of AV block and to further aid in classification of and/or treatment of an arrhythmia. More specifically, as shown in FIG. 13, in a detection block 1304, an implantable stimulation device and/or other device detects a fast ventricular rate. Upon detection of the fast ventricular rate, in a delivery block 1308, the implantable stimulation device delivers a stimulus to alter conduction and/or operation of the AV node and/or the AV bundle (e.g., to induce some degree of AV block). Immediately thereafter, or alternatively after a suitable delay, in another detection block 1312, the implantable stimulation device detects again the ventricular rate. In a logic block 1316, control logic determines whether the rate has diminished due to the delivery of the stimulus (e.g., in block 1308). If the ventricular rate diminished in response to the stimulus, then, in a classification block 1320, the fast ventricular arrhythmia is classified as characteristic of a SVA. Following classification, in an application block 1324, the implantable stimulation device optionally applies antiSVA therapy.

However, if the logic block 1316 determines that the ventricular rate did not diminish, then one or more parameters related to the stimulus are optionally adjusted in a repeat stimulation block 1328, a stimulation power block 1330 and/or a stimulation site block 1332 (or other suitable block(s)). After adjustment of the one or more parameters, a decision block 1336 decides whether one or more limits have been reached. If the decision block 1336 indicates at one or more limits have been reached, then, in a classification block 1340, the fast ventricular rate is classified as a originating from a ventricular arrhythmia. Following classification, in an application block 1344, the implantable stimulation device optionally applies antiVA therapy.

While the foregoing exemplary methods 900, 1000, 1100, 1200, 1300 have been set forth as separate methods, combination of the various blocks within these methods is also possible. In addition, according to various exemplary methods and/or devices, stimulation occurs optionally at a non-epicardial location and/or at an epicardial location. For example, suitable non-epicardial locations include, but are not limited to, right and left cervical vagal locations. Of course, locations also optionally include those associated with afferent parasympathetic pathways.

Various exemplary methods include stimulation of the vagal nerve input to the AV node to create temporary AV block. According to such exemplary methods, the temporary uncoupling of upper and lower chambers of the heart helps in discriminating arrhythmias and/or in determining whether a ventricular arrhythmia is present. As described above, vagal nerve input to the AV node may include the left cervical vagus; hence, in one example, stimulation may occur at a site on or proximate to the left cervical vagus. Other or alternative sites may include endocardial and epicardial sites, which may optionally allow for use of more traditional stimulation leads.

As described, various exemplary methods optionally use one or more stimulation parameters that reduce the risk of producing an evoked response. In general, the strength of the duration curve for nerve is below that of cardiac tissue, which may allow for parasympathetic nerve stimulation on an epicardial aspect of the heart via an endocardial electrode whereby the stimulating does not produce an evoked response. Exemplary parasympathetic stimulation parameters include, but are not limited to, pulse widths on the order of approximately 10 to approximately 500 microseconds, frequencies of approximately 2 to approximately 100 pulses per second and/or duty cycles of approximately 5% or less. To avoid stimulation of other nearby nerves, such as the phrenic nerve, various waveforms are optionally used, for example, a quasitrapezoidal waveform may act to minimize stimulation of other nerves and/or localize stimulation at or near a target nerve.

With respect to stimulation induced, temporary AV block, in the absence of ventricular arrhythmia, ventricular rate may be expected to drop by approximately 40 bpm, depending on specific circumstances; whereas, in the presence of a ventricular arrhythmia, with or without concurrent atrial arrhythmia, the ventricular rate should remain unchanged.

With respect to back-up pacing, an exemplary method optionally delivers one or more stimuli to produce a ventricular evoked response in the case that AV conduction drops and/or ventricular rate drops, for example, below some threshold level of conduction or threshold rate. For example, if stimulation of a parasympathetic nerve caused the ventricular rate to drop below 60 bpm, then back-up pacing or stimuli may be delivered.

Various exemplary methods optionally include implementation of other arrhythmia discrimination techniques before, during and/or after stimulation aimed at affecting AV conduction. For example, a decision tree may call for one or more arrhythmia discrimination techniques that rely on criteria such as suddenness of onset, rate stability, morphology, and motion detection from an accelerometer and then call for implementation of one or more of the various exemplary methods. Again, implementation of stimulation that may cause a decrease in AV conduction may be considered undesirable in an exercising patient experiencing sinus tachycardia only.

Stimulation of Epicardial Nerves and/or Tissue Regions

Figure 14:
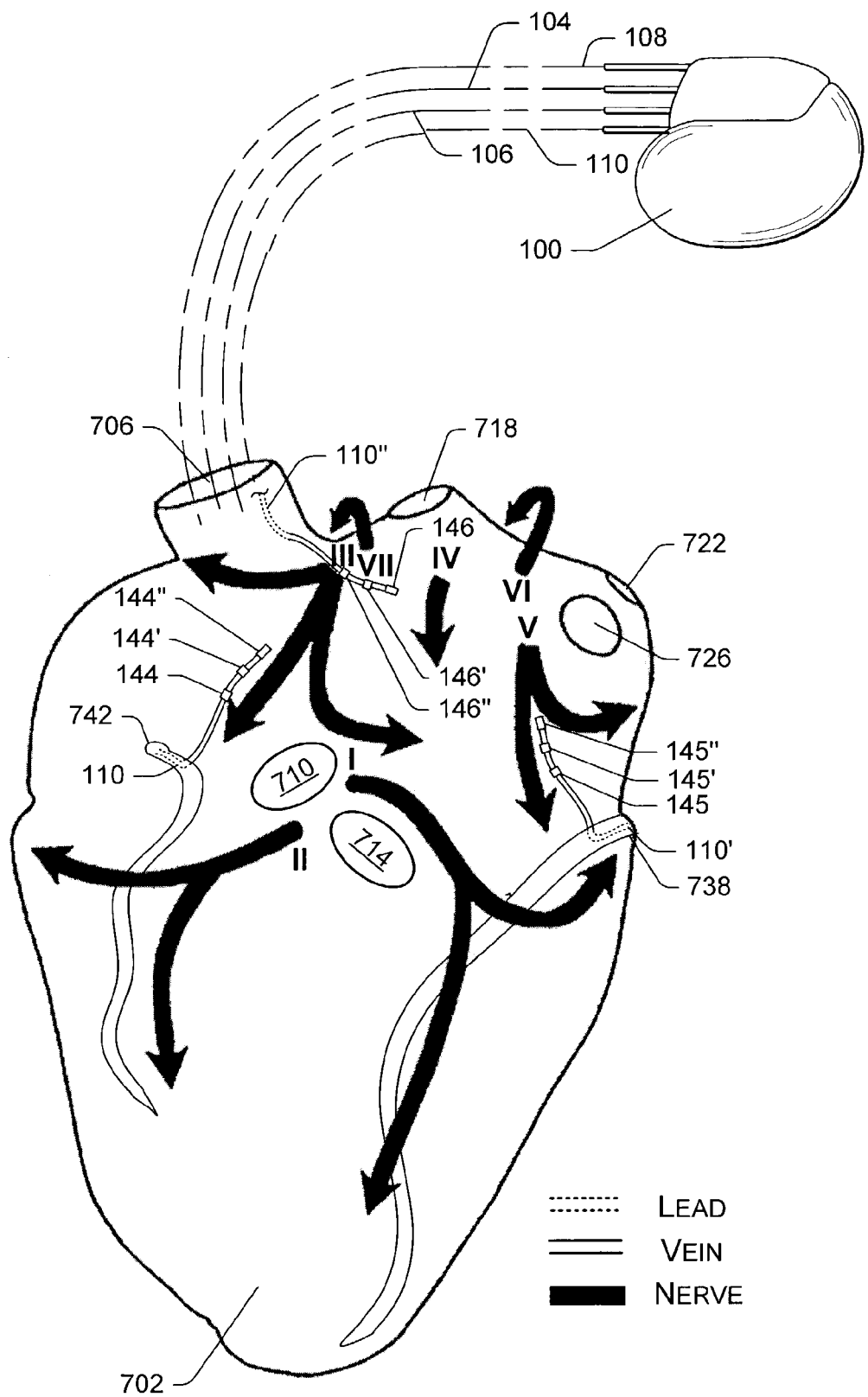
FIG. 14 is an approximate anatomical ventral view diagram of a human heart including some arteries, veins and nerves and stimulation leads associated with a pacing device.

Referring again to FIGS. 7 and 8, various epicardial vessels are shown along with various subplexuses. Referring to FIG. 14, an approximate anatomical diagram of a ventral view of a heart that corresponds to the diagram of FIG. 7 is shown. In FIG. 14, exemplary leads having exemplary electrodes are also shown in exemplary epicardial locations. For example, FIG. 14 shows the exemplary stimulation device 100 of FIG. 1 having four leads 104, 106, 108, 110. The leads 104, 106, 108, 110 optionally include branches or bifurcations. In this example, any of the leads may carry electrodes suitable for stimulation of autonomic nerves. As shown in FIG. 11, one exemplary lead 110 has an electrode portion having three electrodes 144, 144', 144". The electrode portion of the lead 110 passes through the wall of the anterior cardiac vein 742 and extends along nerves emanating from the VRA (III) subplexus. Having an electrode portion of a lead positioned as such, activation of at least one of the electrodes 144, 144', 144" optionally stimulate nerves to release acetylcholine and/or affect operation of the SA node. In a similar manner, another exemplary lead 110' has an electrode portion having three electrodes 145, 145', 145". The electrode portion of the lead 110' passes through the wall of the great cardiac vein 738 and extends along nerves emanating from the LD (V) subplexus. Having an electrode portion of a lead positioned as such, activation of at least one of the electrodes 145, 145', 145" optionally stimulate nerves to release acetylcholine and/or affect operation of the AV node. Yet another exemplary lead 110" has an electrode portion having three electrodes 146, 146', 146". The electrode portion of the lead 110" passes through the wall of the superior vena cava (see, e.g., opening of superior vena cava labeled 706) and extends to the VRA (III) subplexus and/or DRA (VII) subplexus. Having an electrode portion of a lead positioned as such, activation of at least one of the electrodes 146, 146', 146" optionally stimulate nerves to release acetylcholine and/or affect operation of the SA node. Of course, the locations and functions of the three leads 110, 110', 110" are only exemplary as a variety of other arrangements are possible. In general, leads may extend to pre-ganglionated field regions, ganglionated field regions and/or post-ganglionated field regions. More specifically, leads optionally extend to pre-ganglionated field regions, ganglionated field regions and/or post-ganglionated field regions associated with at least one of the seven subplexus identified in the Pauza et al. reference. While the leads shown in FIG. 14 include electrode portions that extend through a vessel and/or chamber wall, other exemplary leads include electrode portions that remain within the lumen of a vessel and/or within a chamber of the heart. Again, such leads optionally extend to pre-ganglionated field regions, ganglionated field regions and/or post-ganglionated field regions associated with at least one of the seven subplexus identified in the Pauza et al. reference. Further, exemplary leads optionally include electrode portions that remain within the lumen of a vessel and/or within a chamber of the heart.

Figure 15:
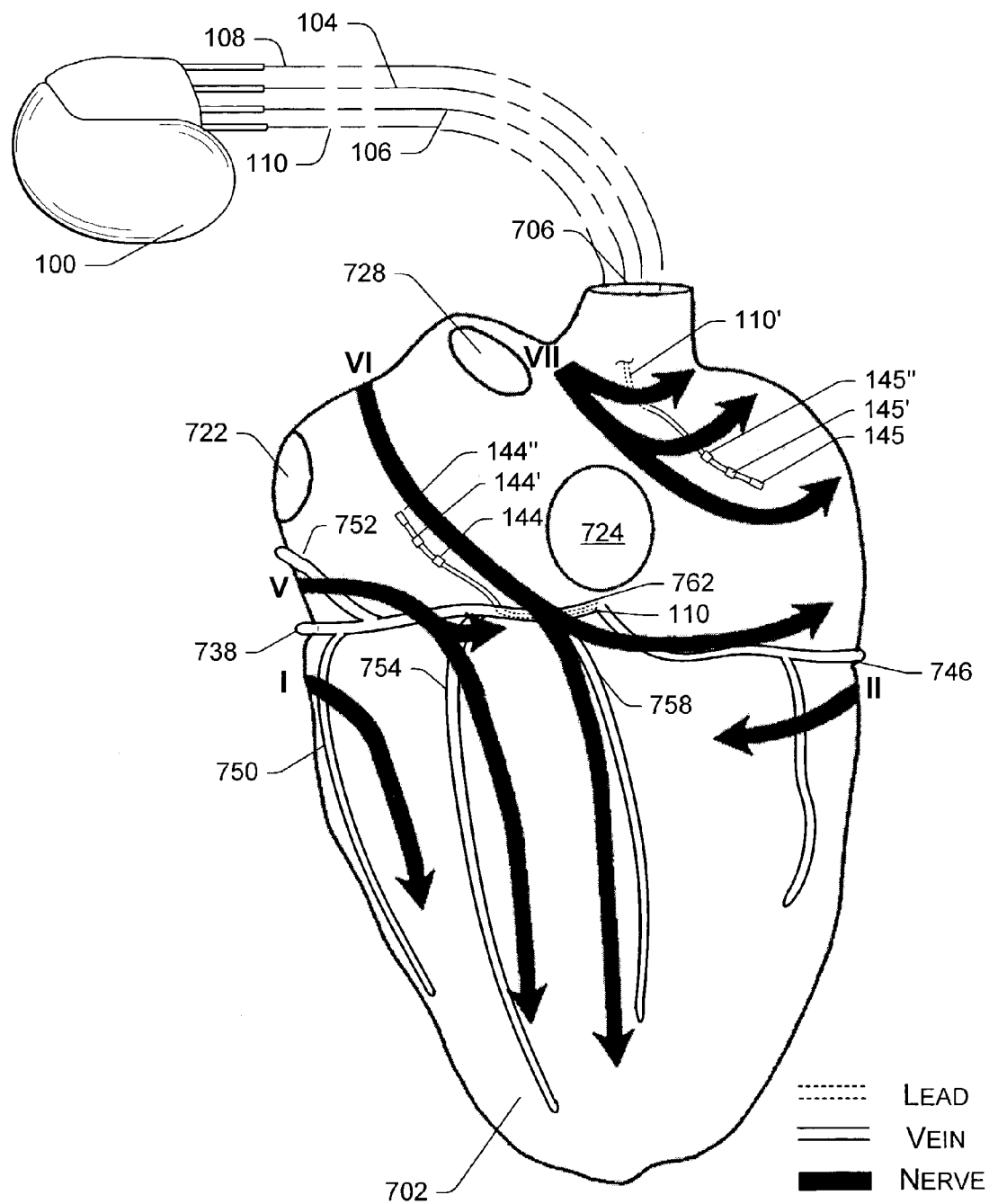
FIG. 15 is an approximate anatomical dorsal view diagram of a human heart including some arteries, veins and nerves and stimulation leads associated with a pacing device.

Referring to FIG. 15, an approximate anatomical diagram of a ventral view of a heart that corresponds to the diagram of FIG. 8 is shown. FIG. 15 shows the exemplary stimulation device 100 of FIG. 1 having four leads 104, 106, 108, 110. The leads 104, 106, 108, 110 optionally include branches or bifurcations. In this example, any of the leads may carry electrodes suitable for stimulation of autonomic nerves. As shown in FIG. 15, one exemplary lead 110 has an electrode portion having three electrodes 144, 144', 144". The electrode portion of the lead 110 passes through the wall of the coronary sinus 662 and extends along nerves emanating from the MD (VI) subplexus and/or LD (V) subplexus. Having an electrode portion of a lead positioned as such, activation of at least one of the electrodes 144, 144', 144" may stimulate nerves to release acetylcholine and/or affect operation of the AV node. In a similar manner, another exemplary lead 110' has an electrode portion having three electrodes 145, 145', 145". The electrode portion of the lead 110' passes through the wall of the superior vena cava (see, e.g., opening of superior vena cava labeled 706) and extends to the DRA (VII) subplexus and/or to nerves emanating from the DRA (VII) subplexus. Having an electrode portion of a lead positioned as such, activation of at least one of the electrodes 145, 145', 145" may stimulate nerves to release acetylcholine and/or affect operation of the SA node. Of course, the locations and functions of the two leads 110, 110' are only exemplary as a variety of other arrangements are possible. In general, leads may extend to pre-ganglionated field regions, ganglionated field regions and/or post-ganglionated field regions. More specifically, leads optionally extend to pre-ganglionated field regions, ganglionated field regions and/or post-ganglionated field regions associated with at least one of the seven subplexus identified in the Pauza et al. reference.

Figure 16:
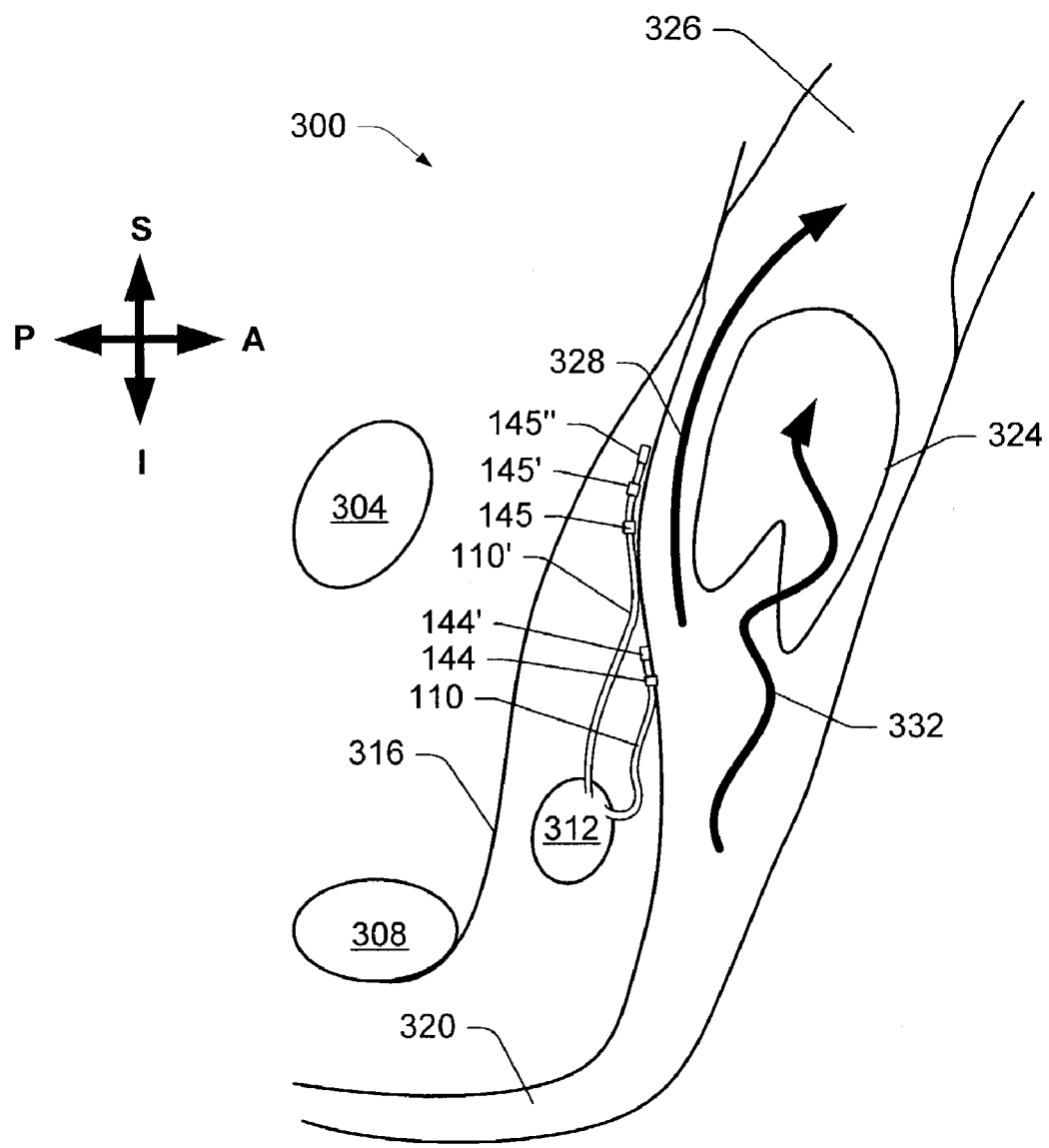
FIG. 16 is an approximate anatomical diagram of an AV nodal region including exemplary leads and/or electrode portions.

Referring to FIG. 16, the approximate anatomical diagram 300 of FIG. 3 is shown along with two electrode portions 110, 110'. In this exemplary method, the electrode portions 110, 110' access the right atrium via a patient's coronary sinus 312. One electrode portion 110 is positioned inferior to the approximate AV node 324 and the other electrode portion 110' is positioned approximately along the inferior-superior axis at approximately the same position as the AV node 324. Yet another electrode portion is optionally positioned superior to the AV node 324 along the AV bundle region 326. Of course, an exemplary method may include one or more electrode portions positioned inferior, equal and/or superior to the AV node 324. In general, an electrode portion is positioned posterior to the AV node 324; however, other positioning is within the scope of various exemplary methods.

The electrode portions 110, 110' have one or more corresponding electrodes. For example, the electrode portion 110 includes a ring electrode 144 and a distal tip electrode 144'. Similarly, the electrode portion 110' includes two ring electrodes 145, 145' and a distal tip electrode 145". The various electrodes and/or electrode portions are optionally secured via cauterization means, anchoring means, etc. For instance, cauterization means optionally includes heating at least part of the electrode portion to secure the electrode portion to tissue. Anchoring means optionally includes screws, biasing prong(s), hooks, etc.

According to the diagram of FIG. 16, a stimulation device is configured to deliver stimulation pulses to the electrode portions 110, 110'. Further, the stimulation device optionally determines whether to shunt or induce "fast" and/or "slow" pathway conduction. The stimulation device is optionally configured to affect operation and/or conduction of the AV node and/or AV bundle via exemplary electrode portions 110, 110'. Of course, a stimulation device optionally stimulates nerves and/or tissue at such locations and/or at other locations.

As already mentioned, an electrode may be positioned proximate to the AV node and/or AV bundle and used to deliver stimuli to decrease conduction in the AV node and/or to cause an evoked response of one or more chambers of the heart. Such an electrode may be used in a manner to cause an evoked response when target myocardium is not refractory and to decrease conduction in the AV node when the target myocardium is refractory. Of course, such an electrode may stimulate a parasympathetic nerve that acts to decrease AV nodal conduction as well. Various exemplary methods optionally use such an electrode to achieve a desired decrease in AV conduction and/or to stimulate a chamber of the heart. In various exemplary methods, one or more stimulation parameters are chosen to selectively stimulate AV nodal tissue to reduce conduction (e.g., refractoriness, tetanus, fatigue, etc.), a parasympathetic nerve to cause release of acetylcholine and/or to effectuate a brain response and/or myocardium in a manner sufficient to cause an evoked response. In general, tetanus is a state of continuous muscular contraction that may be induced via relatively rapid and repeated stimuli and fatigue is due to a lack of energy and/or a build up of waste products. Fatigue may be classified as twitch fatigue (e.g., due to a series of contractions that do not cause a state of tetanus) or tetanus fatigue (e.g., due to a state of tetanus).

While FIGS. 14, 15 and 16 show electrode portions and/or leads labeled "110", such electrode portions and/or leads optionally stem from the leads 104, 106, 108 of the stimulation device 100, as shown in FIG. 1.

According to various exemplary methods, delivery of one or more stimulation pulses affects conduction and/or operation of an AV node and/or AV bundle. Such exemplary methods optionally include detecting a need for altering conduction and/or operation of the AV node and/or the AV bundle. Such exemplary methods optionally include delivering a stimulation pulse to a first electrode portion having one or more electrodes positioned proximate to the AV node and/or AV bundle and/or delivering a stimulation pulse to a second electrode portion having one or more electrodes positioned proximate to a parasympathetic pathway. In such exemplary methods, delivery of a stimulation pulse to the first electrode portion optionally causes the AV node and/or AV bundle to enter a refractory period and/or delivery of a stimulation pulse to the second electrode portion causes a decrease in conduction through the AV node and/or AV bundle.

Yet another exemplary method includes delivering a stimulation pulse to one electrode portion having one or more electrodes positioned proximate to the AV node and/or AV bundle and proximate to a parasympathetic pathway to cause the AV node and/or AV bundle to enter a refractory period and to reduce conduction of the AV node and/or AV bundle. While yet another exemplary method includes delivering a stimulation pulse to a first electrode portion having one or more electrodes positioned inferior to the AV node and/or delivering a stimulation pulse to a second electrode portion having one or more electrodes positioned equal to and/or superior to the AV node; and delivering a stimulation pulse to a third electrode portion having one or more electrodes positioned proximate to a parasympathetic pathway to reduce conduction of the AV node and/or AV bundle. As explained below, delivering optionally occurs postinspiration.

Various exemplary methods optionally include positioning one or more electrodes in the superior vena cava (SVC), the inferior vena cava (IVC) and/or the coronary sinus (CS). Other sites may include jugular veins or other veins proximate to parasympathetic nerves or pressure sensors that can trigger parasympathetic responses. Various exemplary methods optionally include positioning one or more electrodes in the azygous vein. Suitable electrode portions for positioning electrodes in or near a nerve and/or the heart include, but are not limited to, basket type or double helix type of electrode portions, see, e.g., U.S. patent application Ser. No. 10/321,307, filed Dec. 16, 2002, entitled "Implantable lead and electrode portion", to Helland and Shelchuk, which is incorporated by referenced herein, and U.S. patent application Ser. No. 10/000,333, filed Oct. 22, 2001, entitled "Implantable lead and method for stimulation the vagus nerve", to Weinberg, which is incorporated by reference herein.

In various exemplary methods, stimulation to affect AV conduction aims to avoid producing an evoked response from the myocardium (e.g., contraction of a chamber). In this regard, such stimulation may occur according to a power, frequency, duty cycle, phase (e.g., monophasic, biphasic, triphasic, etc.) that reduces the risk of myocardial stimulation and/or the stimulation may occur during a refractory period of the myocardium to reduce the risk of myocardial stimulation.

Determining Vagal Tone and/or Inspiration/Postinspiration

Figure 17:
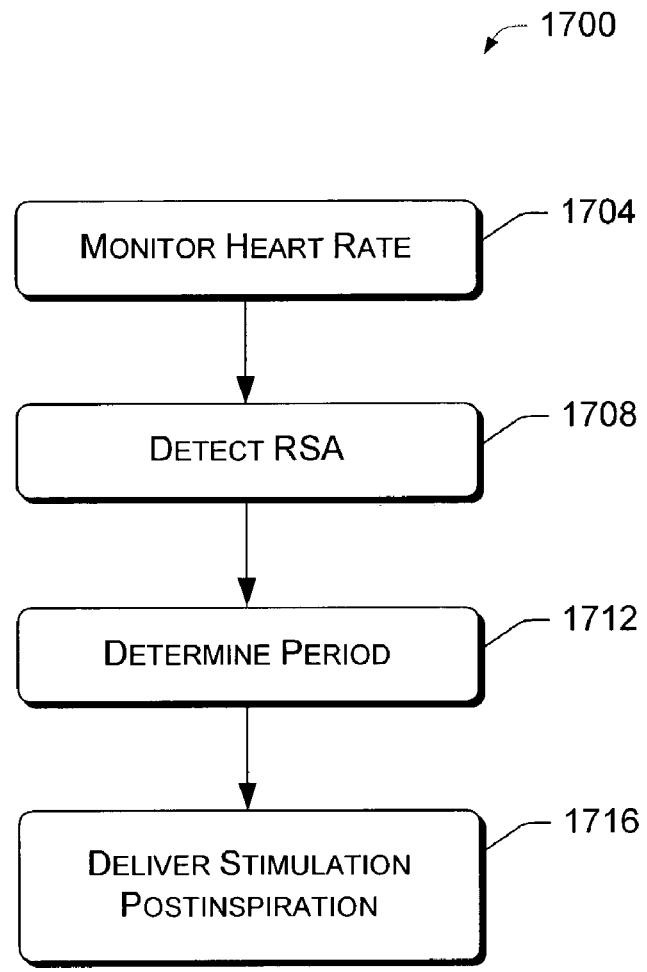
FIG. 17 is a block diagram of an exemplary method for delivering a stimulation pulse postinspiration.

As already mentioned, Mendelowitz noted that "cardiac vagal neurons recorded in vivo receive inhibitory synaptic input during inspiration, which is then followed by a rapid depolarization caused by excitatory synaptic input during postinspiration". Therefore, for a variety of reasons, the aforementioned exemplary methods and/or device optionally stimulate nerves and/or tissue postinspiration, i.e., not during inspiration. Referring to FIG. 17, an exemplary method 1700 for delivery of one or more stimulation pulses postinspiration is shown. In a monitoring block 1704, a stimulation and/or other device monitors directly and/or indirectly heart rate. Next, in a detection block 1708, the stimulation and/or other device detects respiratory sinus arrhythmia. Following detection, in a determination block 1712, the stimulation and/or other device determines a period associated with inspiration. Next, in a delivery block 1716, the stimulation device delivers a stimulation pulse to a nerve and/or tissue region. Also note that such a method can determine a patient's vagal tone.

In another exemplary method, a stimulation and/or other device monitors inspiration directly and/or indirectly through use of a ventilation module and/or sensor. In this exemplary method and the aforementioned method, stimulation pulse delivery during postinspiration only can decrease power demand on an implantable stimulation device. In yet another exemplary method, parasympathetic stimulation pulse delivery occurs during a refractory period to avoid stimulation of cardiac and/or other tissue. Of course, an exemplary combined method optionally includes delivery of a stimulation pulse postinspiration in a refractory period.

Stimulation Postinspiration and/or Synchronous with Heart

Figure 18:
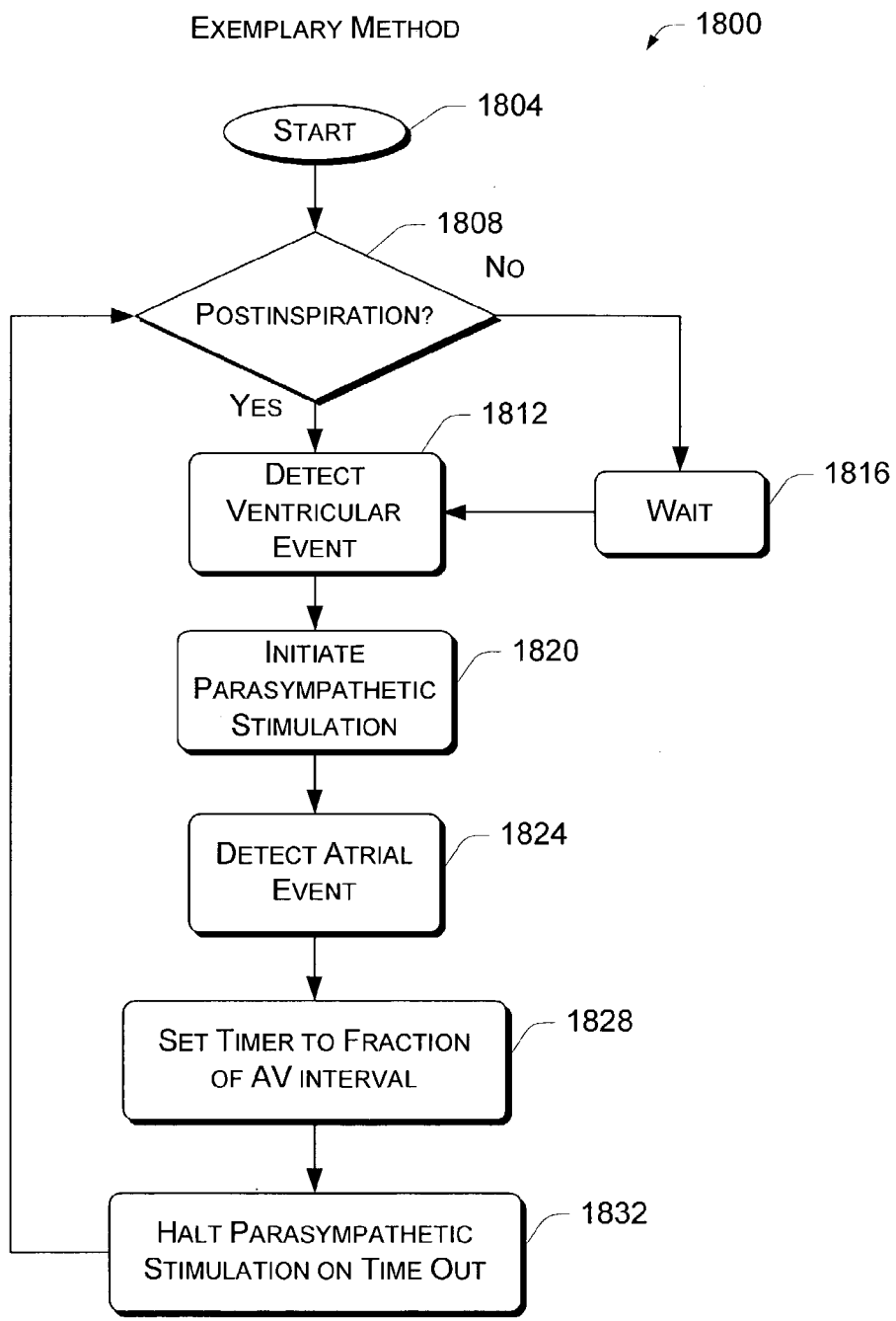
FIG. 18 is a block diagram of an exemplary method for delivering parasympathetic stimulation during a postinspiration phase and/or based on detection of one or more cardiac events.

As already mentioned, stimulation to slow AV conduction (e.g., parasympathetic and/or other stimulation) may occur postinspiration (e.g., not during inspiration) and/or in synchrony with one or more cardiac events (e.g., events typically found in a cardiac cycle). FIG. 18 shows an exemplary method 1800 wherein parasympathetic stimulation occurs according to respiratory cycle and/or according to one or more events in a cardiac cycle. Various exemplary methods presented herein may implement one or more of the blocks or procedures described with reference to the exemplary method 1800.

A start block 1804 may occur at anytime an exemplary method desires to implement parasympathetic nerve stimulation. A decision block 1808 follows that determines whether a patient is in a postinspiration phase of a respiratory cycle. For example, an exemplary device may detect impedance, movement of an implanted device, pressure, cardiac characteristics, autonomic tone, etc., and then use such information to determine one or more phases of a respiratory cycle. In the exemplary method 1800, if the decision block 1808 determines that a patient is not in a postinspiration phase, then the method 1800 may continue in a wait block 1816, which either causes an appropriate delay or waits for an event indicative of a postinspiration phase. If the decision block 1808 determines that a patient is in a postinspiration phase, the method 1800 continues in a ventricular event detection block 1812; the wait block 1816 also continues at the ventricular event detection block 1812. In general, the ventricular event detection block 1812 aims to detect an R wave or a ventricular contraction. As described above, parasympathetic stimulation may act to decrease AV conduction.

Upon detection of a particular event, the method 1800 then initiates parasympathetic stimulation in an initiation block 1820. The stimulation may continue for a set period of time, may continue until detection of another cardiac event or may continue for a certain amount of time based on detection of a subsequent cardiac event. As shown in FIG. 18, the method 1800 includes an atrial event detection block 1824. For example, such a detection block may detect an atrial paced event and/or an intrinsic atrial event. Upon detection of the atrial event, the method 1800 proceeds to set a timer to a fraction of an atrio-ventricular interval or other suitable interval in a set timer block 1828. Upon expiration of the timer, a halt parasympathetic stimulation block 1832 halts parasympathetic stimulation. In this example, parasympathetic stimulation may be halted to ensure that the parasympathetic stimulation does not cause any significant detriment to active contractility. Thereafter, the exemplary method 1800 continues at the decision block 1808, at the detection block 1812 or at another suitable point (e.g., a decision block that decides whether further parasympathetic stimulation is required). Of course, as mentioned above, parasympathetic stimulation may be delivered during a refractory period of the myocardium or a portion thereof that may participate significantly in contraction of a chamber of the heart. Hence, the exemplary method 1800 optionally includes stimulating during a refractory period, for example, to reduce the risk of producing an evoked response from the myocardium.

Selecting and/or Positioning Leads and/or Electrodes

An exemplary method for selecting and/or positioning a lead and/or an electrode is optionally implemented during implantation and/or after implantation. For example, during an implantation procedure, a patient is optionally instrumented to monitor heart function. For example, heart rate may be monitored via an EKG and contractility via arterial pressure sensors (e.g., the time derivative of the pressure can provide a good measure of contractility). In this example, monitoring of cardiac function and/or other functions may occur through use of external instrumentation and/or through use of implanted leads and/or sensors.

Consider a situation wherein parasympathetic tuning via parasympathetic nerve stimulation aims to decrease heart rate and/or to decrease AV conduction. In such a situation, an exemplary method includes adjusting pulse amplitude and/or pulse frequency to relatively high values, automatically or manually (e.g., an implantable device having a lead and/or electrode implantation, selection and/or positioning mode(s)). In this exemplary method, through use of stimulation pulses and monitoring of cardiac function and/or other functions, a lead and/or electrode is positioned during implantation to achieve an optimal and/or a satisfactory decrease in heart rate (e.g., an increase of therapeutic value) and/or decrease in AV conduction. In this exemplary method, for example, a physician may slowly move a lead throughout an appropriate region and deliver pulses until a desired decrease in heart rate and/or decrease in AV conduction is seen maximally via monitoring.

In yet another exemplary method, a lead and/or an electrode are optionally positioned to decrease sympathetic activity while at the same time minimizing stimulation effects on heart rate. Once a "sweet spot" is found, then pulse parameters are optionally adjusted to minimize electrical power consumption, for example, by previously mentioned exemplary methods.

CONCLUSION

Although exemplary methods and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and/or devices.

What is claimed is:

1. A method comprising:
   detecting a first ventricular rate;
   stimulating a parasympathetic nerve associated with the atrio-ventricular node, wherein the stimulating occurs postinspiration only;
   detecting a second ventricular rate; and
   classifying the first ventricular rate based on the first ventricular rate and the second ventricular rate.

2. The method of claim 1, wherein the stimulating includes initiating the stimulating based on a cardiac event.

3. The method of claim 2, wherein the cardiac event comprises an R wave.

4. The method of claim 1, wherein the stimulating includes stimulating at a site selected from one or more sites of the group consisting of superior vena cava, inferior vena cava, and coronary sinus.

5. The method of claim 1, further comprising determining whether the first ventricular rate is abnormal prior to the stimulating.

6. The method of claim 1, further comprising applying antiarrhythmia therapy in response to the classifying.

7. The method of claim 1, wherein the classifying includes classifying the first ventricular rate as characteristic of a supraventricular arrhythmia if the first ventricular rate is greater than the second ventricular rate.

8. The method of claim 1, wherein the classifying includes classifying the first ventricular rate as characteristic of a ventricular arrhythmia if the first ventricular rate is equal to or less than the second ventricular rate.

9. A method comprising:
   detecting a first ventricular rate;
   stimulating a parasympathetic nerve associated with the atrio-ventricular node;
   detecting a second ventricular rate; and
   classifying the first ventricular rate based on the first ventricular rate and the second ventricular rate; and
   wherein the stimulating includes stimulating at a site proximate to an epicardial plexus or subplexus.

10. A method comprising:
    stimulating a parasympathetic nerve associated with the atrio-ventricular node to thereby decrease conduction of the atrio-ventricular node;
    detecting a ventricular rate;
    repeating the stimulating and the detecting until the ventricular rate decreases; and
    classifying the cardiac activity as characteristic of a supraventricular arrhythmia.

11. The method of claim 10, wherein the stimulating includes stimulating the parasympathetic nerve postinspiration only.

12. The method of claim 10, wherein the stimulating includes initiating the stimulating based on a cardiac event.

13. A method comprising:
 detecting a first ventricular rate;
 delivering stimulation at a first site in an effort to decrease AV nodal conduction;
 detecting a second ventricular rate; and
 if the first ventricular rate exceeds the second ventricular rate, classifying the first ventricular rate as characteristic of a supraventricular arrhythmia; otherwise, delivering stimulation at a second site in an effort to decrease AV nodal conduction.

14. The method of claim 13, further comprising applying antiarrhythmia therapy in response to the classifying.

15. The method of claim 13, wherein the delivering includes delivering stimulation to one or more parasympathetic nerves.

16. The method of claim 13, wherein the delivering includes delivering a stimulation pulse to the AV node.

17. The method of claim 13, wherein the stimulating includes stimulating the parasympathetic nerve postinspiration only.

18. The method of claim 13, wherein the stimulating includes initiating the stimulating based on a cardiac event.

19. An apparatus comprising:
 means for detecting a first ventricular rate;
 means for decreasing conduction of the atrio-ventricular node by stimulating a parasympathetic nerve associated with the atrioventricular node at a site proximate to an epicardial plexus or subplexus;
 means for detecting a second ventricular rate; and
 means for classifying the first ventricular rate based on the first ventricular rate and the second ventricular rate.

* * * * *